(12) United States Patent
Pacetti et al.

(10) Patent No.: US 7,258,891 B2
(45) Date of Patent: Aug. 21, 2007

(54) STENT MOUNTING ASSEMBLY AND A METHOD OF USING THE SAME TO COAT A STENT

(75) Inventors: Stephen D. Pacetti, San Jose, CA (US); Plaridel K. Villareal, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/409,410

(22) Filed: Apr. 7, 2003

(65) Prior Publication Data

US 2003/0211230 A1 Nov. 13, 2003

Related U.S. Application Data

(62) Division of application No. 09/896,436, filed on Jun. 28, 2001, now Pat. No. 6,565,659.

(51) Int. Cl.
*A61L 27/00* (2006.01)

(52) U.S. Cl. ............ 427/2.24; 427/2.1; 427/2.28; 427/154; 427/156; 427/282; 427/287; 427/421.1; 427/424; 427/425

(58) Field of Classification Search ........ 427/2.1, 427/2.24, 2.28, 154, 156, 256, 282, 287, 427/421, 424, 425
See application file for complete search history.

(56) References Cited

U.S. PATENT DOCUMENTS

| | | |
|---|---|---|
| 2,072,303 A | 3/1937 | Hermann et al. |
| 2,386,454 A | 10/1945 | Frosch et al. |
| 2,647,017 A | 7/1953 | Coulliette |
| 2,701,559 A | 2/1955 | Cooper |
| 3,288,728 A | 11/1966 | Gorham |
| 3,687,135 A | 8/1972 | Stroganov et al. |
| 3,773,737 A | 11/1973 | Goodman et al. |
| 3,839,743 A | 10/1974 | Schwarcz |
| 3,849,514 A | 11/1974 | Gray, Jr. et al. |
| 3,900,632 A | 8/1975 | Robinson |
| 4,075,045 A | 2/1978 | Rideout |
| 4,104,410 A | 8/1978 | Malecki |
| 4,110,497 A | 8/1978 | Hoel |
| 4,132,357 A | 1/1979 | Blackinton |
| 4,164,524 A | 8/1979 | Ward et al. |
| 4,226,243 A | 10/1980 | Shalaby et al. |
| 4,321,711 A | 3/1982 | Mano |
| 4,323,071 A | 4/1982 | Simpson et al. |
| 4,329,383 A | 5/1982 | Joh |

(Continued)

FOREIGN PATENT DOCUMENTS

CA 2 008 312 7/1990

(Continued)

OTHER PUBLICATIONS

Abstract of RD 455093, Mar. 2002.*

(Continued)

*Primary Examiner*—Erma Cameron
(74) *Attorney, Agent, or Firm*—Squire, Sanders & Dempsey LLP

(57) ABSTRACT

A stent mounting device and a method of coating a stent using the device are provided.

22 Claims, 3 Drawing Sheets

U.S. PATENT DOCUMENTS

| | | |
|---|---|---|
| 4,338,942 A | 7/1982 | Fogarty |
| 4,343,931 A | 8/1982 | Barrows |
| 4,346,028 A | 8/1982 | Griffith |
| 4,439,185 A | 3/1984 | Lundquist |
| 4,489,670 A | 12/1984 | Mosser et al. |
| 4,516,972 A | 5/1985 | Samson |
| 4,529,792 A | 7/1985 | Barrows |
| 4,538,622 A | 9/1985 | Samson et al. |
| 4,554,929 A | 11/1985 | Samson et al. |
| 4,573,470 A | 3/1986 | Samson et al. |
| 4,596,574 A | 6/1986 | Urist |
| 4,599,085 A | 7/1986 | Riess et al. |
| 4,608,984 A | 9/1986 | Fogarty |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Simpson |
| 4,629,563 A | 12/1986 | Wrasidlo ............... 210/500.34 |
| 4,633,873 A | 1/1987 | Dumican et al. |
| 4,638,805 A | 1/1987 | Powell |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Brooks et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz ...................... 128/343 |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,768,507 A | 9/1988 | Fischell et al. |
| 4,774,039 A | 9/1988 | Wrasidlo |
| 4,776,337 A | 10/1988 | Palmaz |
| 4,800,882 A | 1/1989 | Gianturco .................. 128/343 |
| 4,816,339 A | 3/1989 | Tu et al. |
| 4,818,559 A | 4/1989 | Hama et al. |
| 4,828,561 A | 5/1989 | Woodroof |
| 4,850,999 A | 7/1989 | Planck |
| 4,865,870 A | 9/1989 | Hu et al. |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |
| 4,882,168 A | 11/1989 | Casey et al. |
| 4,886,062 A | 12/1989 | Wiktor ...................... 128/343 |
| 4,902,289 A | 2/1990 | Yannas |
| 4,906,423 A | 3/1990 | Frisch ......................... 264/48 |
| 4,931,287 A | 6/1990 | Bae et al. |
| 4,932,353 A | 6/1990 | Kawata et al. |
| 4,941,870 A | 7/1990 | Okada et al. |
| 4,943,346 A | 7/1990 | Mattelin |
| 4,950,227 A | 8/1990 | Savin et al. |
| 4,955,899 A * | 9/1990 | Della Corna et al. ...... 623/1.46 |
| 4,967,606 A | 11/1990 | Wells et al. |
| 4,977,901 A | 12/1990 | Ofstead |
| 4,988,356 A | 1/1991 | Crittenden et al. |
| 4,994,033 A | 2/1991 | Shockey et al. |
| 4,994,298 A | 2/1991 | Yasuda |
| 4,994,560 A | 2/1991 | Kruper, Jr. et al. |
| 5,015,505 A | 5/1991 | Cetnar |
| 5,019,090 A | 5/1991 | Pinchuk |
| 5,019,096 A | 5/1991 | Fox, Jr. et al. |
| 5,028,597 A | 7/1991 | Kodama et al. |
| 5,037,392 A | 8/1991 | Hillstead |
| 5,037,427 A | 8/1991 | Harada et al. .............. 606/108 |
| 5,040,548 A | 8/1991 | Yock |
| 5,047,050 A | 9/1991 | Arpesani |
| 5,049,132 A | 9/1991 | Shaffer et al. |
| 5,053,048 A | 10/1991 | Pinchuk |
| 5,059,166 A | 10/1991 | Fischell |
| 5,059,169 A | 10/1991 | Zilber |
| 5,059,211 A | 10/1991 | Stack et al. |
| 5,062,829 A | 11/1991 | Pryor et al. |
| 5,064,435 A | 11/1991 | Porter |
| 5,078,720 A | 1/1992 | Burton et al. |
| 5,081,394 A | 1/1992 | Morishita et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,087,394 A | 2/1992 | Keith |
| 5,100,429 A | 3/1992 | Sinofsky et al. |
| 5,100,992 A | 3/1992 | Cohn et al. |
| 5,102,402 A | 4/1992 | Dror et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,318 A | 5/1992 | Hillstead |
| 5,116,365 A | 5/1992 | Hillstead |
| 5,123,917 A | 6/1992 | Lee |
| 5,127,362 A | 7/1992 | Iwatsu et al. |
| 5,133,742 A | 7/1992 | Pinchuk |
| 5,134,192 A | 7/1992 | Feijen et al. |
| 5,147,370 A | 9/1992 | McNamara et al. |
| 5,156,623 A | 10/1992 | Hakamatsuka et al. |
| 5,156,911 A | 10/1992 | Stewart |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,171,445 A | 12/1992 | Zepf ...................... 210/500.27 |
| 5,176,638 A | 1/1993 | Don Michael |
| 5,188,734 A | 2/1993 | Zepf .......................... 210/490 |
| 5,192,311 A | 3/1993 | King et al. |
| 5,197,977 A | 3/1993 | Hoffman, Jr. et al. |
| 5,205,822 A | 4/1993 | Johnson et al. |
| 5,213,561 A | 5/1993 | Weinstein et al. |
| 5,213,576 A | 5/1993 | Abiuso et al. |
| 5,219,980 A | 6/1993 | Swidler |
| 5,222,971 A | 6/1993 | Willard et al. |
| 5,225,750 A | 7/1993 | Higuchi et al. |
| 5,226,889 A | 7/1993 | Sheiban |
| 5,226,913 A | 7/1993 | Pinchuk |
| 5,229,045 A | 7/1993 | Soldani ........................ 264/41 |
| 5,229,172 A | 7/1993 | Cahalan et al. |
| 5,232,444 A | 8/1993 | Just et al. |
| 5,234,456 A | 8/1993 | Silvestrini |
| 5,234,457 A | 8/1993 | Andersen .................... 606/198 |
| 5,236,447 A | 8/1993 | Kubo et al. |
| 5,242,399 A | 9/1993 | Lau et al. |
| 5,254,089 A | 10/1993 | Wang |
| 5,254,091 A | 10/1993 | Aliahmad et al. |
| 5,258,020 A | 11/1993 | Froix |
| 5,258,419 A | 11/1993 | Rolando et al. |
| 5,269,802 A | 12/1993 | Garber |
| 5,272,012 A | 12/1993 | Opolski |
| 5,278,200 A | 1/1994 | Coury et al. |
| 5,279,594 A | 1/1994 | Jackson |
| 5,282,823 A | 2/1994 | Schwartz et al. |
| 5,282,860 A | 2/1994 | Matsuno et al. |
| 5,286,254 A | 2/1994 | Shapland et al. |
| 5,289,831 A | 3/1994 | Bosley |
| 5,290,271 A | 3/1994 | Jernberg |
| 5,292,516 A | 3/1994 | Viegas et al. |
| 5,298,260 A | 3/1994 | Viegas et al. |
| 5,300,295 A | 4/1994 | Viegas et al. |
| 5,304,200 A | 4/1994 | Spaulding |

| | | | | | | |
|---|---|---|---|---|---|---|
| 5,306,250 A | 4/1994 | March et al. | | 5,527,337 A | 6/1996 | Stack et al. |
| 5,306,286 A | 4/1994 | Stack et al. | | 5,537,729 A | 7/1996 | Kolobow .................. 29/527.2 |
| 5,306,294 A | 4/1994 | Winston et al. | | 5,538,493 A | 7/1996 | Gerken et al. |
| 5,306,501 A | 4/1994 | Viegas et al. | | 5,545,209 A | 8/1996 | Roberts et al. |
| 5,306,786 A | 4/1994 | Moens et al. | | 5,545,408 A | 8/1996 | Trigg et al. |
| 5,308,641 A | 5/1994 | Cahalan et al. | | 5,551,954 A | 9/1996 | Buscemi et al. |
| 5,314,472 A | 5/1994 | Fontaine | | 5,554,120 A | 9/1996 | Chen et al. |
| 5,318,531 A | 6/1994 | Leone | | 5,554,182 A | 9/1996 | Dinh et al. |
| 5,328,471 A | 7/1994 | Slepian | | 5,556,413 A | 9/1996 | Lam |
| 5,330,500 A | 7/1994 | Song | | 5,558,642 A | 9/1996 | Schweich, Jr. et al. |
| 5,330,768 A | 7/1994 | Park et al. | | 5,562,728 A | 10/1996 | Lazarus et al. |
| 5,336,518 A | 8/1994 | Narayanan et al. | | 5,569,463 A | 10/1996 | Helmus et al. |
| 5,342,283 A | 8/1994 | Good | | 5,571,135 A | 11/1996 | Fraser et al. |
| 5,342,348 A | 8/1994 | Kaplan | | 5,571,166 A | 11/1996 | Dinh et al. |
| 5,342,395 A | 8/1994 | Jarrett et al. | | 5,571,567 A | 11/1996 | Shah |
| 5,342,621 A | 8/1994 | Eury | | 5,578,046 A | 11/1996 | Liu et al. |
| 5,344,426 A | 9/1994 | Lau et al. | | 5,578,073 A | 11/1996 | Haimovich et al. |
| 5,344,455 A | 9/1994 | Keogh et al. | | 5,584,877 A | 12/1996 | Miyake et al. |
| 5,350,800 A | 9/1994 | Verhoeven et al. | | 5,588,962 A | 12/1996 | Nicholas et al. |
| 5,356,433 A | 10/1994 | Rowland et al. | | 5,591,199 A | 1/1997 | Porter et al. |
| 5,360,401 A | 11/1994 | Turnland et al. | | 5,591,224 A | 1/1997 | Schwartz et al. |
| 5,360,443 A | 11/1994 | Barone et al. | | 5,591,227 A | 1/1997 | Dinh et al. |
| 5,364,354 A | 11/1994 | Walker et al. | | 5,591,607 A | 1/1997 | Gryaznov et al. |
| 5,366,504 A | 11/1994 | Andersen et al. | | 5,593,403 A | 1/1997 | Buscemi |
| 5,368,560 A | 11/1994 | Rambo et al. | | 5,593,434 A | 1/1997 | Williams |
| 5,370,684 A | 12/1994 | Vallana et al. | | 5,595,722 A | 1/1997 | Grainger et al. |
| 5,380,299 A | 1/1995 | Fearnot et al. | | 5,599,301 A | 2/1997 | Jacobs et al. |
| 5,383,925 A | 1/1995 | Schmitt | | 5,599,307 A | 2/1997 | Bacher et al. |
| 5,383,927 A | 1/1995 | DeGoicoechea et al. | | 5,599,352 A | 2/1997 | Dinh et al. |
| 5,385,580 A | 1/1995 | Schmitt | | 5,599,922 A | 2/1997 | Gryaznov et al. |
| 5,387,450 A | 2/1995 | Stewart | | 5,605,696 A | 2/1997 | Eury et al. |
| 5,389,106 A | 2/1995 | Tower | | 5,607,442 A | 3/1997 | Fischell et al. |
| 5,399,666 A | 3/1995 | Ford | | 5,607,467 A | 3/1997 | Froix |
| 5,405,472 A | 4/1995 | Leone | | 5,609,629 A | 3/1997 | Fearnot et al. |
| 5,409,495 A | 4/1995 | Osborn | | 5,610,241 A | 3/1997 | Lee et al. |
| 5,411,466 A | 5/1995 | Hess | | 5,611,775 A | 3/1997 | Machold et al. ............... 604/53 |
| 5,411,477 A | 5/1995 | Saab | | 5,616,338 A | 4/1997 | Fox, Jr. et al. |
| 5,412,035 A | 5/1995 | Schmitt et al. | | 5,618,298 A | 4/1997 | Simon |
| 5,415,938 A | 5/1995 | Cahalan et al. | | 5,618,299 A | 4/1997 | Khosravi et al. |
| 5,417,981 A | 5/1995 | Endo et al. | | 5,620,420 A | 4/1997 | Kriesel |
| 5,423,849 A | 6/1995 | Engelson et al. | | 5,624,411 A | 4/1997 | Tuch .......................... 604/265 |
| 5,423,885 A | 6/1995 | Williams | | 5,628,730 A | 5/1997 | Shapland et al. |
| 5,429,618 A | 7/1995 | Keogh | | 5,628,755 A | 5/1997 | Heller et al. |
| 5,441,515 A | 8/1995 | Khosravi et al. | | 5,628,781 A | 5/1997 | Williams et al. |
| 5,443,458 A | 8/1995 | Eury et al. | | 5,628,785 A | 5/1997 | Schwartz et al. |
| 5,443,496 A | 8/1995 | Schwartz et al. | | 5,628,786 A | 5/1997 | Banas et al. .................... 623/1 |
| 5,443,500 A | 8/1995 | Sigwart | | 5,629,077 A | 5/1997 | Turnlund et al. |
| 5,445,646 A | 8/1995 | Euteneuer et al. | | 5,631,135 A | 5/1997 | Gryaznov et al. |
| 5,447,724 A | 9/1995 | Helmus et al. | | 5,632,771 A | 5/1997 | Boatman et al. |
| 5,451,233 A | 9/1995 | Yock | | 5,632,840 A | 5/1997 | Campbell |
| 5,455,040 A | 10/1995 | Marchant | | 5,637,113 A | 6/1997 | Tartaglia et al. |
| 5,456,661 A | 10/1995 | Narciso, Jr. | | 5,644,020 A | 7/1997 | Timmermann et al. |
| 5,456,713 A | 10/1995 | Chuter | | 5,645,559 A | 7/1997 | Hachtman et al. |
| 5,458,615 A | 10/1995 | Klemm et al. | | 5,649,951 A | 7/1997 | Davidson |
| 5,460,610 A | 10/1995 | Don Michael | | 5,649,977 A | 7/1997 | Campbell |
| 5,462,990 A | 10/1995 | Hubbell et al. | | 5,653,691 A | 8/1997 | Rupp et al. |
| 5,464,450 A | 11/1995 | Buscemi et al. | | 5,656,080 A | 8/1997 | Staniforth et al. |
| 5,464,650 A | 11/1995 | Berg et al. | | 5,656,082 A | 8/1997 | Takatsuki et al. |
| 5,470,313 A | 11/1995 | Crocker et al. | | 5,658,995 A | 8/1997 | Kohn et al. |
| 5,470,603 A | 11/1995 | Staniforth et al. | | 5,667,523 A | 9/1997 | Bynon et al. |
| 5,476,476 A | 12/1995 | Hillstead | | 5,667,767 A | 9/1997 | Greff et al. |
| 5,476,509 A | 12/1995 | Keogh et al. | | 5,667,796 A | 9/1997 | Otten |
| 5,485,496 A | 1/1996 | Lee et al. | | 5,670,558 A | 9/1997 | Onishi et al. |
| 5,496,346 A | 3/1996 | Horzewski et al. | | 5,674,242 A | 10/1997 | Phan et al. |
| 5,500,013 A | 3/1996 | Buscemi et al. | | 5,679,400 A | 10/1997 | Tuch |
| 5,501,227 A | 3/1996 | Yock | | 5,693,085 A | 12/1997 | Buirge et al. |
| 5,502,158 A | 3/1996 | Sinclair et al. | | 5,693,376 A | 12/1997 | Fetherston et al. |
| 5,507,768 A | 4/1996 | Lau et al. | | 5,695,498 A | 12/1997 | Tower |
| 5,511,726 A | 4/1996 | Greenspan et al. | | 5,695,810 A | 12/1997 | Dubin et al. |
| 5,514,154 A | 5/1996 | Lau et al. | | 5,697,967 A | 12/1997 | Dinh et al. |
| 5,514,379 A | 5/1996 | Weissleder et al. | | 5,700,286 A | 12/1997 | Tartaglia et al. |
| 5,516,560 A | 5/1996 | Harayama et al. | | 5,702,754 A | 12/1997 | Zhong |
| 5,516,881 A | 5/1996 | Lee et al. | | 5,702,818 A | 12/1997 | Cahalan et al. |

| | | | | | | |
|---|---|---|---|---|---|---|
| 5,707,385 A | 1/1998 | Williams | | 5,840,083 A | 11/1998 | Braach-Maksvytis |
| 5,711,763 A | 1/1998 | Nonami et al. | | 5,843,033 A | 12/1998 | Ropiak |
| 5,711,812 A | 1/1998 | Chapek et al. | | 5,843,119 A | 12/1998 | Schulewitz |
| 5,711,958 A | 1/1998 | Cohn et al. | | 5,843,172 A | 12/1998 | Yan |
| 5,713,949 A | 2/1998 | Jayaraman | | 5,846,247 A | 12/1998 | Unsworth et al. |
| 5,716,981 A | 2/1998 | Hunter et al. | | 5,849,859 A | 12/1998 | Acemoglu |
| 5,718,726 A | 2/1998 | Amon et al. | | 5,851,508 A | 12/1998 | Greff et al. |
| 5,720,726 A | 2/1998 | Marcadis et al. | | 5,853,408 A | 12/1998 | Muni |
| 5,721,131 A | 2/1998 | Rudolph et al. | | 5,854,207 A | 12/1998 | Lee et al. |
| 5,722,984 A | 3/1998 | Fischell et al. | | 5,854,376 A | 12/1998 | Higashi |
| 5,723,219 A | 3/1998 | Kolluri et al. | | 5,855,598 A | 1/1999 | Pinchuk .................... 623/1 |
| 5,725,549 A | 3/1998 | Lam | | 5,855,612 A | 1/1999 | Ohthuki et al. |
| 5,726,297 A | 3/1998 | Gryaznov et al. | | 5,855,618 A | 1/1999 | Patnaik et al. |
| 5,728,068 A | 3/1998 | Leone et al. | | 5,857,998 A | 1/1999 | Barry |
| 5,728,751 A | 3/1998 | Patnaik | | 5,858,556 A | 1/1999 | Eckert et al. |
| 5,730,698 A | 3/1998 | Fischell et al. | | 5,858,746 A | 1/1999 | Hubbell et al. |
| 5,733,326 A | 3/1998 | Tomonto et al. | | 5,858,990 A | 1/1999 | Walsh |
| 5,733,327 A | 3/1998 | Igaki et al. | | 5,860,954 A | 1/1999 | Ropiak |
| 5,733,330 A | 3/1998 | Cox | | 5,865,814 A | 2/1999 | Tuch ..................... 604/265 |
| 5,733,564 A | 3/1998 | Lehtinen | | 5,866,113 A | 2/1999 | Hendriks et al. |
| 5,733,925 A | 3/1998 | Kunz et al. | | 5,868,781 A | 2/1999 | Killion |
| 5,735,897 A | 4/1998 | Buirge | | 5,869,127 A | 2/1999 | Zhong |
| 5,741,554 A | 4/1998 | Tisone | | 5,871,436 A | 2/1999 | Eury |
| 5,741,881 A | 4/1998 | Patnaik | | 5,871,437 A | 2/1999 | Alt |
| 5,746,745 A | 5/1998 | Abele et al. | | 5,873,904 A | 2/1999 | Ragheb et al. |
| 5,746,998 A | 5/1998 | Torchilin et al. | | 5,874,101 A | 2/1999 | Zhong et al. |
| 5,756,457 A | 5/1998 | Wang et al. | | 5,874,109 A | 2/1999 | Ducheyne et al. |
| 5,756,476 A | 5/1998 | Epstein et al. | | 5,874,165 A | 2/1999 | Drumheller |
| 5,759,205 A | 6/1998 | Valentini | | 5,874,355 A | 2/1999 | Huang et al. |
| 5,759,474 A | 6/1998 | Rupp et al. | | 5,876,426 A | 3/1999 | Kume et al. |
| 5,765,682 A | 6/1998 | Bley et al. | | 5,876,433 A | 3/1999 | Lunn |
| 5,766,204 A | 6/1998 | Porter et al. | | 5,876,743 A | 3/1999 | Ibsen et al. |
| 5,766,239 A | 6/1998 | Cox | | 5,877,224 A | 3/1999 | Brocchini et al. |
| 5,766,710 A | 6/1998 | Turnlund et al. | | 5,877,263 A | 3/1999 | Patnaik et al. |
| 5,769,883 A | 6/1998 | Buscemi et al. | | 5,879,713 A | 3/1999 | Roth et al. |
| 5,769,884 A | 6/1998 | Solovay | | 5,883,011 A | 3/1999 | Lin et al. |
| 5,770,609 A | 6/1998 | Grainger et al. | | 5,888,533 A | 3/1999 | Dunn |
| 5,772,864 A | 6/1998 | M.o slashed.ller et al. ... 205/73 | | 5,891,192 A | 4/1999 | Murayama et al. |
| 5,776,184 A | 7/1998 | Tuch | | 5,893,840 A | 4/1999 | Hull et al. |
| 5,780,807 A | 7/1998 | Saunders | | 5,893,852 A | 4/1999 | Morales |
| 5,782,742 A | 7/1998 | Crocker et al. | | 5,895,407 A | 4/1999 | Jayaraman ................. 606/198 |
| 5,783,657 A | 7/1998 | Pavlin et al. | | 5,897,911 A | 4/1999 | Loeffler .................... 427/2.25 |
| 5,788,626 A | 8/1998 | Thompson ................... 600/36 | | 5,897,955 A | 4/1999 | Drumheller |
| 5,788,979 A | 8/1998 | Alt et al. | | 5,898,178 A | 4/1999 | Bunker |
| 5,800,392 A | 9/1998 | Racchini | | 5,902,631 A | 5/1999 | Wang et al. |
| 5,800,516 A | 9/1998 | Fine et al. | | 5,902,875 A | 5/1999 | Roby et al. |
| 5,804,318 A | 9/1998 | Pinchuk et al. | | 5,905,168 A | 5/1999 | Dos Santos et al. |
| 5,807,244 A | 9/1998 | Barot | | 5,906,759 A | 5/1999 | Richter |
| 5,810,871 A | 9/1998 | Tuckey et al. | | 5,910,564 A | 6/1999 | Gruning et al. |
| 5,810,873 A | 9/1998 | Morales | | 5,914,182 A | 6/1999 | Drumheller |
| 5,811,151 A | 9/1998 | Hendriks et al. | | 5,914,387 A | 6/1999 | Roby et al. |
| 5,811,447 A | 9/1998 | Kunz et al. | | 5,916,234 A | 6/1999 | Lam |
| 5,820,917 A | 10/1998 | Tuch .......................... 427/2.1 | | 5,916,870 A | 6/1999 | Lee et al. |
| 5,823,996 A | 10/1998 | Sparks ......................... 604/96 | | 5,919,893 A | 7/1999 | Roby et al. |
| 5,824,048 A | 10/1998 | Tuch | | 5,921,416 A | 7/1999 | Uchara |
| 5,824,049 A | 10/1998 | Ragheb et al. | | 5,922,005 A | 7/1999 | Richter et al. |
| 5,824,056 A | 10/1998 | Rosenberg | | 5,922,393 A | 7/1999 | Jayaraman ................. 427/2.3 |
| 5,826,586 A | 10/1998 | Mishra et al. | | 5,925,552 A | 7/1999 | Keogh et al. |
| 5,830,178 A | 11/1998 | Jones et al. | | 5,925,720 A | 7/1999 | Kataoka et al. |
| 5,830,179 A | 11/1998 | Mikus et al. | | 5,928,916 A | 7/1999 | Keogh |
| 5,830,217 A | 11/1998 | Ryan | | 5,932,299 A | 8/1999 | Katoot |
| 5,830,461 A | 11/1998 | Billiar | | 5,935,135 A | 8/1999 | Bramfitt et al. ............. 606/108 |
| 5,830,879 A | 11/1998 | Isner | | 5,942,209 A | 8/1999 | Leavitt et al. |
| 5,833,644 A | 11/1998 | Zadno-Azizi et al. | | 5,947,993 A | 9/1999 | Morales |
| 5,833,651 A | 11/1998 | Donovan et al. | | 5,948,018 A | 9/1999 | Dereume et al. ............... 623/1 |
| 5,833,659 A | 11/1998 | Kranys ......................... 604/96 | | 5,948,428 A | 9/1999 | Lee et al. |
| 5,834,582 A | 11/1998 | Sinclair et al. | | 5,951,881 A | 9/1999 | Rogers et al. |
| 5,836,962 A | 11/1998 | Gianotti | | 5,954,744 A | 9/1999 | Phan et al. |
| 5,836,965 A | 11/1998 | Jendersee et al. | | 5,955,509 A | 9/1999 | Webber et al. |
| 5,837,008 A | 11/1998 | Berg et al. | | 5,957,975 A | 9/1999 | Lafont et al. |
| 5,837,313 A | 11/1998 | Ding et al. | | 5,958,385 A | 9/1999 | Tondeur et al. |
| 5,837,835 A | 11/1998 | Gryaznov et al. | | 5,962,138 A | 10/1999 | Kolluri et al. |
| 5,840,009 A | 11/1998 | Fischell et al. | | 5,965,720 A | 10/1999 | Gryaznov et al. |

| | | | | | |
|---|---|---|---|---|---|
| 5,968,091 A | 10/1999 | Pinchuk et al. | 6,113,629 A | 9/2000 | Ken |
| 5,968,092 A | 10/1999 | Buscemi et al. | 6,117,479 A | 9/2000 | Hogan et al. |
| 5,969,422 A | 10/1999 | Ting et al. | 6,117,979 A | 9/2000 | Hendriks et al. |
| 5,971,954 A | 10/1999 | Conway et al. | 6,120,477 A | 9/2000 | Campbell et al. |
| 5,972,027 A | 10/1999 | Johnson | 6,120,491 A | 9/2000 | Kohn et al. |
| 5,972,029 A | 10/1999 | Fuisz | 6,120,535 A | 9/2000 | McDonald et al. |
| 5,972,505 A | 10/1999 | Phillips et al. | 6,120,536 A | 9/2000 | Ding et al. |
| 5,976,155 A | 11/1999 | Foreman et al. | 6,120,788 A | 9/2000 | Barrows |
| 5,976,182 A | 11/1999 | Cox | 6,120,847 A | 9/2000 | Yang et al. .................. 427/335 |
| 5,980,564 A | 11/1999 | Stinson | 6,120,904 A | 9/2000 | Hostettler et al. |
| 5,980,928 A | 11/1999 | Terry | 6,121,027 A | 9/2000 | Clapper et al. |
| 5,980,972 A | 11/1999 | Ding | 6,123,712 A | 9/2000 | Di Caprio et al. |
| 5,981,568 A | 11/1999 | Kunz et al. | 6,125,523 A | 10/2000 | Brown et al. |
| 5,984,449 A | 11/1999 | Tajika et al. | 6,126,686 A | 10/2000 | Badylak et al. ............ 612/1.24 |
| 5,986,169 A | 11/1999 | Gjunter | 6,127,173 A | 10/2000 | Eckstein et al. |
| 5,997,468 A | 12/1999 | Wolff et al. | 6,129,761 A | 10/2000 | Hubbell |
| 5,997,517 A | 12/1999 | Whitbourne | 6,129,928 A | 10/2000 | Sarangapani et al. |
| 6,010,445 A | 1/2000 | Armini et al. | 6,132,809 A | 10/2000 | Hynes et al. |
| 6,010,530 A | 1/2000 | Goicoechea | 6,136,333 A | 10/2000 | Cohn et al. |
| 6,010,573 A | 1/2000 | Bowlin ....................... 118/620 | 6,140,127 A | 10/2000 | Sprague |
| 6,011,125 A | 1/2000 | Lohmeijer et al. | 6,140,431 A | 10/2000 | Kinker et al. |
| 6,013,099 A | 1/2000 | Dinh et al. | 6,143,354 A | 11/2000 | Koulik et al. |
| 6,015,541 A | 1/2000 | Greff et al. | 6,143,370 A | 11/2000 | Panagiotou et al. |
| 6,019,789 A | 2/2000 | Dinh et al. | 6,149,574 A | 11/2000 | Trauthen et al. |
| 6,024,918 A | 2/2000 | Hendriks et al. | 6,150,630 A | 11/2000 | Perry et al. |
| 6,027,510 A | 2/2000 | Alt | 6,153,252 A * | 11/2000 | Hossainy et al. ............ 427/2.3 |
| 6,027,526 A | 2/2000 | Limon et al. | 4,776,337 A | 12/2000 | Palmaz |
| 6,030,371 A | 2/2000 | Pursley | 6,156,373 A | 12/2000 | Zhong et al. ............... 427/2.28 |
| 6,033,582 A | 3/2000 | Lee et al. | 6,159,227 A | 12/2000 | Di Caprio et al. |
| 6,033,719 A | 3/2000 | Keogh | 6,159,229 A | 12/2000 | Jendersee et al. |
| 6,034,204 A | 3/2000 | Mohr et al. | 6,159,951 A | 12/2000 | Karpeisky et al. |
| 6,042,606 A | 3/2000 | Frantzen | 6,159,978 A | 12/2000 | Myers et al. |
| 6,042,875 A | 3/2000 | Ding et al. | 6,160,084 A | 12/2000 | Langer et al. |
| 6,045,899 A | 4/2000 | Wang et al. ............ 428/315.7 | 6,165,212 A | 12/2000 | Dereume et al. |
| 6,048,964 A | 4/2000 | Lee et al. | 6,166,130 A | 12/2000 | Rhee et al. |
| 6,051,021 A | 4/2000 | Frid | 6,168,617 B1 | 1/2001 | Blaeser et al. |
| 6,051,576 A | 4/2000 | Ashton et al. | 6,168,619 B1 | 1/2001 | Dinh et al. |
| 6,051,648 A | 4/2000 | Rhee et al. | 6,169,170 B1 | 1/2001 | Gryaznov et al. |
| 6,054,553 A | 4/2000 | Groth et al. | 6,171,609 B1 | 1/2001 | Kunz |
| 6,056,906 A | 5/2000 | Werneth et al. | 6,172,167 B1 | 1/2001 | Stapert et al. |
| 6,056,993 A | 5/2000 | Leidner et al. ............ 427/2.25 | 6,174,316 B1 | 1/2001 | Tuckey et al. |
| 6,059,752 A | 5/2000 | Segal | 6,174,330 B1 | 1/2001 | Stinson |
| 6,059,810 A | 5/2000 | Brown et al. | 6,177,523 B1 | 1/2001 | Reich et al. |
| 6,060,451 A | 5/2000 | DiMaio et al. | 6,180,632 B1 | 1/2001 | Myers et al. |
| 6,060,518 A | 5/2000 | Kabanov et al. | 6,183,505 B1 | 2/2001 | Mohn, Jr. et al. |
| 6,063,092 A | 5/2000 | Shin | 6,187,045 B1 | 2/2001 | Fehring et al. |
| 6,066,156 A | 5/2000 | Yan | 6,193,727 B1 | 2/2001 | Foreman et al. |
| 6,071,266 A | 6/2000 | Kelley | 6,203,551 B1 | 3/2001 | Wu |
| 6,071,305 A | 6/2000 | Brown et al. | 6,209,621 B1 | 4/2001 | Treacy |
| 6,074,659 A | 6/2000 | Kunz et al. | 6,210,715 B1 | 4/2001 | Starling et al. |
| 6,080,099 A | 6/2000 | Slater et al. | 6,211,249 B1 | 4/2001 | Cohn et al. |
| 6,080,177 A | 6/2000 | Igaki et al. | 6,214,115 B1 | 4/2001 | Taylor et al. ................ 118/423 |
| 6,080,190 A | 6/2000 | Schwartz | 6,214,407 B1 | 4/2001 | Laube et al. |
| 6,080,488 A | 6/2000 | Hostettler et al. | 6,214,901 B1 | 4/2001 | Chudzik et al. |
| 6,083,258 A | 7/2000 | Yadav | 6,217,586 B1 | 4/2001 | Mackenzie |
| 6,086,610 A | 7/2000 | Duerig et al. | 6,217,721 B1 | 4/2001 | Xu et al. |
| 6,090,330 A | 7/2000 | Gawa et al. | 6,224,626 B1 | 5/2001 | Steinke |
| 6,093,199 A | 7/2000 | Brown et al. | 6,224,675 B1 | 5/2001 | Prentice et al. |
| 6,093,463 A | 7/2000 | Thakrar | 6,224,894 B1 | 5/2001 | Jamiolkowski et al. |
| 6,096,070 A | 8/2000 | Ragheb et al. | 6,228,845 B1 | 5/2001 | Donovan et al. |
| 6,096,525 A | 8/2000 | Patnaik | 6,231,590 B1 | 5/2001 | Slaikeu et al. |
| 6,099,455 A | 8/2000 | Columbo et al. | 6,231,600 B1 | 5/2001 | Zhong |
| 6,099,559 A | 8/2000 | Nolting | 6,240,616 B1 | 6/2001 | Yan |
| 6,099,561 A | 8/2000 | Alt | 6,242,041 B1 | 6/2001 | Katoot et al. |
| 6,099,562 A | 8/2000 | Ding et al. | 6,245,076 B1 | 6/2001 | Yan |
| 6,103,230 A | 8/2000 | Billiar et al. | 6,245,099 B1 | 6/2001 | Edwin et al. ............... 623/1.13 |
| 6,106,454 A | 8/2000 | Berg et al. | 6,245,103 B1 | 6/2001 | Stinson |
| 6,106,530 A | 8/2000 | Harada | 6,245,753 B1 | 6/2001 | Byun et al. |
| 6,106,889 A | 8/2000 | Beavers et al. | 6,245,760 B1 | 6/2001 | He et al. |
| 6,107,416 A | 8/2000 | Patnaik et al. | 6,248,129 B1 | 6/2001 | Froix |
| 6,110,180 A | 8/2000 | Foreman et al. | 6,248,344 B1 | 6/2001 | Ylanen et al. |
| 6,110,188 A | 8/2000 | Narciso, Jr. | 6,251,135 B1 | 6/2001 | Stinson et al. |
| 6,110,483 A | 8/2000 | Whitbourne et al. | 6,251,136 B1 | 6/2001 | Guruwaiya et al. |

| Patent No. | Date | Inventor |
|---|---|---|
| 6,251,142 B1 | 6/2001 | Bernacca et al. |
| 6,253,443 B1 | 7/2001 | Johnson |
| 6,254,632 B1 | 7/2001 | Wu et al. |
| 6,258,099 B1 | 7/2001 | Mareiro et al. |
| 6,258,121 B1 | 7/2001 | Yang et al. ............... 623/1.46 |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,850 B1 | 8/2001 | Gambale |
| 6,273,913 B1 | 8/2001 | Wright et al. |
| 6,277,110 B1 | 8/2001 | Morales |
| 6,277,449 B1 | 8/2001 | Kolluri et al. |
| 6,279,368 B1 | 8/2001 | Escano et al. ............. 72/342.1 |
| 6,281,262 B1 | 8/2001 | Shikinami |
| 6,283,947 B1 | 9/2001 | Mirzaee |
| 6,283,949 B1 | 9/2001 | Roorda |
| 6,284,305 B1 | 9/2001 | Ding et al. |
| 6,284,333 B1 | 9/2001 | Wang et al. |
| 6,287,332 B1 | 9/2001 | Bolz et al. |
| 6,287,628 B1 | 9/2001 | Hossainy et al. |
| 6,290,721 B1 | 9/2001 | Heath |
| 6,293,966 B1 | 9/2001 | Frantzen |
| 6,294,836 B1 | 9/2001 | Paranjpe et al. |
| 6,296,603 B1 | 10/2001 | Turnlund et al. |
| 6,299,604 B1 | 10/2001 | Ragheb et al. |
| 6,303,901 B1 | 10/2001 | Perry et al. |
| 6,306,176 B1 | 10/2001 | Whitbourne |
| 6,312,459 B1 | 11/2001 | Huang et al. |
| 6,319,520 B1 | 11/2001 | Wuthrich et al. |
| 6,322,588 B1 | 11/2001 | Ogle et al. |
| 6,322,847 B1 | 11/2001 | Zhong et al. ............. 427/2.28 |
| 6,327,772 B1 | 12/2001 | Zadno-Azizi et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,362,099 B1 | 3/2002 | Gandikota et al. |
| 6,364,903 B2 | 4/2002 | Tseng et al. ............... 623/1.15 |
| 6,375,458 B1 | 4/2002 | Moorleghem et al. |
| 6,375,826 B1 | 4/2002 | Wang et al. |
| 6,379,379 B1 | 4/2002 | Wang |
| 6,379,381 B1 | 4/2002 | Hossainy et al. |
| 6,387,118 B1 | 5/2002 | Hanson ...................... 623/1.11 |
| 6,387,121 B1 | 5/2002 | Alt |
| 6,387,379 B1 | 5/2002 | Goldberg et al. |
| 6,388,043 B1 | 5/2002 | Langer et al. |
| 6,395,325 B1 | 5/2002 | Hedge et al. |
| 6,395,326 B1 | 5/2002 | Castro et al. |
| 6,406,738 B1 | 6/2002 | Hogan et al. |
| 6,409,761 B1 | 6/2002 | Jang |
| 6,413,272 B1 | 7/2002 | Igaki |
| 6,419,692 B1 | 7/2002 | Yang et al. |
| 6,420,189 B1 | 7/2002 | Lopatin |
| 6,423,092 B2 | 7/2002 | Datta et al. |
| 6,436,816 B1 | 8/2002 | Lee et al. |
| 6,444,567 B1 | 9/2002 | Besser et al. |
| 6,447,835 B1 | 9/2002 | Wang et al. |
| 6,451,373 B1 | 9/2002 | Hossainy et al. |
| 6,454,738 B1 | 9/2002 | Tran et al. |
| 6,455,424 B1 | 9/2002 | McTeer et al. |
| 6,461,632 B1 | 10/2002 | Gogolewski |
| 6,462,284 B1 | 10/2002 | Hashimoto |
| 6,464,720 B2 | 10/2002 | Boatman et al. |
| 6,468,906 B1 | 10/2002 | Chan et al. |
| 6,479,565 B1 | 11/2002 | Stanley |
| 6,481,262 B2 | 11/2002 | Ching et al. |
| 6,482,834 B2 | 11/2002 | Spada et al. |
| 6,485,512 B1 | 11/2002 | Cheng |
| 6,488,701 B1 | 12/2002 | Nolting et al. |
| 6,488,773 B1 | 12/2002 | Ehrhardt et al. |
| 6,491,666 B1 | 12/2002 | Santini, Jr. et al. |
| 6,492,615 B1 | 12/2002 | Flanagan |
| 6,494,862 B1 | 12/2002 | Ray et al. |
| 6,494,908 B1 | 12/2002 | Huxel et al. |
| 6,495,156 B2 | 12/2002 | Wenz et al. |
| 6,495,200 B1 | 12/2002 | Chan et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,504,307 B1 | 1/2003 | Malik et al. |
| 6,506,437 B1 | 1/2003 | Harish et al. |
| 6,510,722 B1 | 1/2003 | Ching et al. |
| 6,511,748 B1 | 1/2003 | Barrows |
| 6,517,888 B1 | 2/2003 | Weber |
| 6,517,889 B1 | 2/2003 | Jayaraman |
| 6,521,284 B1 | 2/2003 | Parsons et al. ............. 427/2.24 |
| 6,524,232 B1 | 2/2003 | Tang et al. |
| 6,524,347 B1 | 2/2003 | Myers et al. |
| 6,527,801 B1 | 3/2003 | Dutta |
| 6,527,863 B1 | 3/2003 | Pacetti et al. ................ 118/500 |
| 6,528,526 B1 | 3/2003 | Myers et al. |
| 6,530,950 B1 | 3/2003 | Alvarado et al. |
| 6,530,951 B1 | 3/2003 | Bates et al. |
| 6,537,589 B1 | 3/2003 | Chae et al. |
| 6,539,607 B1 | 4/2003 | Fehring et al. |
| 6,540,776 B2 | 4/2003 | Sanders Millare et al. |
| 6,540,777 B2 | 4/2003 | Stenzel |
| 6,544,223 B1 | 4/2003 | Kokish |
| 6,544,543 B1 | 4/2003 | Mandrusov et al. |
| 6,544,582 B1 | 4/2003 | Yoe |
| 6,554,758 B2 | 4/2003 | Turnlund et al. |
| 6,554,854 B1 | 4/2003 | Flanagan |
| 6,555,059 B1 | 4/2003 | Myrick et al. |
| 6,555,157 B1 | 4/2003 | Hossainy |
| 6,558,733 B1 | 5/2003 | Hossainy et al. |
| 6,562,136 B1 | 5/2003 | Chappa et al. |
| 6,565,599 B1 | 5/2003 | Hong et al. |
| 6,565,659 B1 | 5/2003 | Pacetti et al. |
| 6,569,191 B1 | 5/2003 | Hogan |
| 6,569,193 B1 | 5/2003 | Cox et al. |
| 6,572,644 B1 | 6/2003 | Moein |
| 6,572,672 B2 | 6/2003 | Yadav et al. |
| 6,574,851 B1 | 6/2003 | Mirizzi |
| 6,582,417 B1 | 6/2003 | Ledesma et al. |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,592,614 B2 | 7/2003 | Lenker et al. |
| 6,592,617 B2 | 7/2003 | Thompson |
| 6,596,296 B1 | 7/2003 | Nelson et al. |
| 6,605,114 B1 | 8/2003 | Yan et al. |
| 6,605,154 B1 | 8/2003 | Villareal |
| 6,605,874 B2 | 8/2003 | Leu et al. |
| 6,610,087 B1 * | 8/2003 | Zarbatany et al. ......... 623/1.32 |
| 6,613,072 B2 | 9/2003 | Lau et al. |
| 6,616,765 B1 | 9/2003 | Hossainy et al. |
| 6,623,448 B2 | 9/2003 | Slater |
| 6,625,486 B2 | 9/2003 | Lundkvist et al. |
| 6,626,939 B1 | 9/2003 | Burnside et al. |
| 6,635,269 B1 | 10/2003 | Jennissen |
| 6,635,964 B2 | 10/2003 | Maex et al. |
| 6,645,135 B1 | 11/2003 | Bhat |
| 6,645,195 B1 | 11/2003 | Bhat et al. |
| 6,645,243 B2 | 11/2003 | Vallana et al. |
| 6,645,547 B1 | 11/2003 | Shekalim et al. |
| 6,656,162 B2 | 12/2003 | Santini, Jr. et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,664,187 B1 | 12/2003 | Ngo et al. |
| 6,664,335 B2 | 12/2003 | Krishnan |
| 6,666,214 B2 | 12/2003 | Canham |
| 6,666,880 B1 | 12/2003 | Chiu et al. |

| | | | | | | |
|---|---|---|---|---|---|---|
| 6,667,049 B2 | 12/2003 | Janas et al. | | 2002/0087123 A1 | 7/2002 | Hossainy et al. |
| 6,669,723 B2 | 12/2003 | Killion et al. | | 2002/0091433 A1 | 7/2002 | Ding et al. |
| 6,669,980 B2 | 12/2003 | Hansen | | 2002/0094440 A1 | 7/2002 | Llanos et al. |
| 6,673,154 B1 | 1/2004 | Pacetti et al. | | 2002/0111590 A1 | 8/2002 | Davila et al. |
| 6,673,385 B1 | 1/2004 | Ding et al. | | 2002/0116050 A1 | 8/2002 | Kocur |
| 6,676,697 B1 | 1/2004 | Richter | | 2002/0120326 A1 | 8/2002 | Michal |
| 6,676,700 B1 * | 1/2004 | Jacobs et al. ............... 623/1.34 | | 2002/0138133 A1 | 9/2002 | Lenz et al. |
| 6,679,980 B1 | 1/2004 | Andreacchi | | 2002/0142039 A1 | 10/2002 | Claude |
| 6,689,099 B2 | 2/2004 | Mirzaee | | 2002/0155212 A1 | 10/2002 | Hossainy |
| 6,689,375 B1 | 2/2004 | Wahlig et al. | | 2002/0161114 A1 | 10/2002 | Gunatillake et al. |
| 6,695,920 B1 | 2/2004 | Pacetti et al. | | 2002/0165608 A1 | 11/2002 | Llanos et al. |
| 6,703,307 B2 | 3/2004 | Lopatin et al. | | 2002/0176849 A1 | 11/2002 | Slepian |
| 6,706,013 B1 | 3/2004 | Bhat et al. | | 2002/0183581 A1 | 12/2002 | Yoe et al. |
| 6,706,273 B1 | 3/2004 | Roessler | | 2002/0187632 A1 | 12/2002 | Marsh |
| 6,709,379 B1 | 3/2004 | Brandau et al. | | 2002/0188037 A1 | 12/2002 | Chudzik et al. |
| 6,709,514 B1 | 3/2004 | Hossainy | | 2002/0188277 A1 | 12/2002 | Roorda et al. |
| 6,712,845 B2 | 3/2004 | Hossainy | | 2003/0003221 A1 | 1/2003 | Zhong et al. |
| 6,713,119 B2 | 3/2004 | Hossainy et al. | | 2003/0004141 A1 | 1/2003 | Brown |
| 6,716,444 B1 | 4/2004 | Castro et al. | | 2003/0028243 A1 | 2/2003 | Bates et al. |
| 6,719,934 B2 | 4/2004 | Stinson | | 2003/0028244 A1 | 2/2003 | Bates et al. |
| 6,719,989 B1 | 4/2004 | Matsushima et al. | | 2003/0031780 A1 | 2/2003 | Chudzik et al. |
| 6,720,402 B2 | 4/2004 | Langer et al. | | 2003/0032767 A1 | 2/2003 | Tada et al. |
| 6,723,120 B2 | 4/2004 | Yan | | 2003/0033001 A1 | 2/2003 | Igaki |
| 6,733,768 B2 | 5/2004 | Hossainy et al. | | 2003/0036794 A1 | 2/2003 | Ragheb et al. |
| 6,740,040 B1 | 5/2004 | Mandrusov et al. | | 2003/0039689 A1 | 2/2003 | Chen et al. |
| 6,743,462 B1 | 6/2004 | Pacetti | | 2003/0040712 A1 | 2/2003 | Ray et al. |
| 6,746,773 B2 | 6/2004 | Llanos et al. | | 2003/0040790 A1 | 2/2003 | Furst |
| 6,749,626 B1 | 6/2004 | Bhat et al. | | 2003/0054090 A1 | 3/2003 | Hansen |
| 6,752,826 B2 | 6/2004 | Holloway et al. | | 2003/0055482 A1 | 3/2003 | Schwager et al. |
| 6,753,007 B2 | 6/2004 | Haggard et al. | | 2003/0059520 A1 | 3/2003 | Chen et al. |
| 6,753,071 B1 | 6/2004 | Pacetti | | 2003/0060877 A1 | 3/2003 | Falotico et al. |
| 6,758,859 B1 | 7/2004 | Dang et al. | | 2003/0065377 A1 | 4/2003 | Davila et al. |
| 6,759,054 B2 | 7/2004 | Chen et al. | | | | |
| 6,764,505 B1 | 7/2004 | Hossainy et al. | | FOREIGN PATENT DOCUMENTS | | |
| 6,774,278 B1 | 8/2004 | Ragheb et al. | | CA | 2 007 648 | 4/1991 |
| 6,776,792 B1 | 8/2004 | Yan et al. | | CA | 1 322 628 | 10/1993 |
| 6,783,793 B1 | 8/2004 | Hossainy et al. | | CA | 1 336 319 | 7/1995 |
| 6,818,063 B1 | 11/2004 | Kerrigan | | CA | 1 338 303 | 5/1996 |
| 6,846,323 B2 | 1/2005 | Yip et al. | | DE | 042 24 401 | 1/1994 |
| 6,860,946 B2 | 3/2005 | Hossainy et al. | | DE | 044 07 079 | 9/1994 |
| 6,861,088 B2 | 3/2005 | Weber et al. | | DE | 197 31 021 | 9/1994 |
| 6,865,810 B2 | 3/2005 | Stinson | | DE | 199 16 086 | 10/1999 |
| 6,869,443 B2 | 3/2005 | Buscemi et al. | | DE | 198 56 983 | 12/1999 |
| 6,878,160 B2 | 4/2005 | Gilligan et al. | | EP | 0 108 171 | 5/1984 |
| 6,887,270 B2 | 5/2005 | Miller et al. | | EP | 0 144 534 | 6/1985 |
| 6,887,485 B2 | 5/2005 | Fitzhugh et al. | | EP | 0 301 856 | 2/1989 |
| 6,890,546 B2 | 5/2005 | Mollison et al. | | EP | 0 380 668 | 4/1989 |
| 6,899,731 B2 | 5/2005 | Li et al. | | EP | 0 351 314 | 1/1990 |
| 2001/0007083 A1 | 7/2001 | Roorda | | EP | 0 364 787 | 4/1990 |
| 2001/0014717 A1 | 8/2001 | Hossainy et al. | | EP | 0 396 429 | 11/1990 |
| 2001/0016753 A1 | 8/2001 | Caprio et al. | | EP | 0 397 500 | 11/1990 |
| 2001/0020011 A1 | 9/2001 | Mathiowitz et al. | | EP | 0 464 755 | 1/1992 |
| 2001/0029351 A1 | 10/2001 | Falotico et al. | | EP | 0 493 788 | 7/1992 |
| 2001/0037145 A1 * | 11/2001 | Guruwaiya et al. ........ 623/1.15 | | EP | 0 526 606 | 9/1992 |
| 2001/0044652 A1 | 11/2001 | Moore | | EP | 0 514 406 | 11/1992 |
| 2001/0051608 A1 | 12/2001 | Mathiowitz et al. | | EP | 0 517 075 | 12/1992 |
| 2002/0002399 A1 | 1/2002 | Huxel et al. | | EP | 0 540 290 | 5/1993 |
| 2002/0004060 A1 | 1/2002 | Heublein et al. | | EP | 0 553 960 | 8/1993 |
| 2002/0004101 A1 | 1/2002 | Ding et al. | | EP | 0 554 082 | 8/1993 |
| 2002/0005206 A1 | 1/2002 | Falotico et al. | | EP | 0 565 251 | 10/1993 |
| 2002/0007213 A1 | 1/2002 | Falotico et al. | | EP | 0 578 998 | 1/1994 |
| 2002/0007214 A1 | 1/2002 | Falotico | | EP | 0 604 022 | 6/1994 |
| 2002/0007215 A1 | 1/2002 | Falotico et al. | | EP | 0 621 017 | 10/1994 |
| 2002/0009604 A1 | 1/2002 | Zamora et al. | | EP | 0 623 354 | 11/1994 |
| 2002/0016625 A1 | 2/2002 | Falotico et al. | | EP | 0 627 226 | 12/1994 |
| 2002/0032414 A1 | 3/2002 | Ragheb et al. | | EP | 0 649 637 | 4/1995 |
| 2002/0032434 A1 | 3/2002 | Chudzik et al. | | EP | 0 665 023 | 8/1995 |
| 2002/0051730 A1 | 5/2002 | Bodnar et al. | | EP | 0 701 802 | 3/1996 |
| 2002/0062148 A1 | 5/2002 | Hart | | EP | 0 701 803 | 3/1996 |
| 2002/0065553 A1 | 5/2002 | Weber | | EP | 0 709 068 | 5/1996 |
| 2002/0071822 A1 | 6/2002 | Uhrich | | EP | 0 716 836 | 6/1996 |
| 2002/0077693 A1 | 6/2002 | Barclay et al. | | EP | 0 732 087 | 9/1996 |
| 2002/0082679 A1 | 6/2002 | Sirhan et al. | | | | |

| | | |
|---|---|---|
| EP | 0 832 618 | 9/1996 |
| EP | 0 756 853 | 2/1997 |
| EP | 0 809 999 | 12/1997 |
| EP | 0 832 655 | 4/1998 |
| EP | 0 834 293 | 4/1998 |
| EP | 0 850 604 | 7/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 972 498 | 1/2000 |
| EP | 0 974 315 | 1/2000 |
| EP | 0 982 041 | 3/2000 |
| EP | 1 023 879 | 8/2000 |
| EP | 1 034 752 | 9/2000 |
| EP | 1 075 838 | 2/2001 |
| EP | 1 103 234 | 5/2001 |
| EP | 1 192 957 | 4/2002 |
| EP | 1 273 314 | 1/2003 |
| EP | 0 869 847 | 3/2003 |
| FR | 2 753 907 | 4/1998 |
| GB | 2 247 696 | 3/1992 |
| GB | 2 316 086 | 1/2000 |
| GB | 2 316 342 | 1/2000 |
| GB | 2 333 975 | 1/2000 |
| GB | 2 336 551 | 1/2000 |
| GB | 2 356 586 | 5/2001 |
| GB | 2 356 587 | 5/2001 |
| GB | 2 333 474 | 6/2001 |
| GB | 2 334 685 | 6/2001 |
| GB | 2 356 585 | 7/2001 |
| GB | 2 374 302 | 8/2001 |
| GB | 2 370 243 | 6/2002 |
| JP | SHO 49-48336 | 12/1974 |
| JP | SHO 54-1831O | 7/1979 |
| JP | 60-28504 | 7/1985 |
| JP | 21199867 | 5/1994 |
| JP | HEI 8-33718 | 2/1996 |
| JP | HEI 10-151190 | 6/1998 |
| JP | 2919971 B2 | 7/1999 |
| JP | 2001-190687 | 7/2001 |
| SU | 0872531 | 10/1981 |
| SU | 0876663 | 10/1981 |
| SU | 0905228 | 2/1982 |
| SU | 0790725 | 2/1983 |
| SU | 1016314 | 5/1983 |
| SU | 0811750 | 9/1983 |
| SU | 1293510 | 2/1987 |
| SU | 1477423 | 5/1989 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/11176 | 8/1991 |
| WO | WO 91/12846 | 9/1991 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/09760 | 5/1994 |
| WO | WO 94/21196 | 9/1994 |
| WO | WO 95/10989 | 4/1995 |
| WO | WO 95/11817 | 5/1995 |
| WO | WO 95/24929 | 9/1995 |
| WO | WO 95/26947 | 11/1995 |
| WO | WO 95/33422 | 12/1995 |
| WO | WO 96/28115 | 9/1996 |
| WO | WO 96/35516 | 11/1996 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/04415 | 2/1998 |
| WO | WO 98/07390 | 2/1998 |
| WO | WO 98/08463 | 3/1998 |
| WO | WO 98/17331 | 4/1998 |
| WO | WO 98/20863 | 5/1998 |
| WO | WO 98/23228 | 6/1998 |
| WO | WO 98/32398 | 7/1998 |
| WO | WO 98/36784 | 8/1998 |
| WO | WO 99/01118 | 1/1999 |
| WO | WO 99/03515 | 1/1999 |
| WO | WO 99/16386 | 4/1999 |
| WO | WO 99/38546 | 8/1999 |
| WO | WO 99/42147 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17459 | 3/2001 |
| WO | WO 01/17577 | 3/2001 |
| WO | WO 01/43727 | 6/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/026162 | 4/2002 |
| WO | WO 02/034311 | 5/2002 |
| WO | WO 02/47731 | 6/2002 |
| WO | WO 02/049771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/037222 | 5/2003 |

OTHER PUBLICATIONS

Angioplasty.org., *Balloons and Stents*, http://www.ptca.org/devices04.html, printed Oct. 15, 2004, 2 pages.

Anonymous, *Capillary Action*, http://www.ndt-ed.org/EducationResources/CommunityCollege/PenetrantTest/Introduction/Keywords/pt1.htm, printed Aug. 12, 2005, 1 page.

Anonymous, *Capillary Force Lithography* (CFL), Nano Processing and Organic Devices Lab, 2 pages (no date).

Anonymous, *Capillary Rise of Liquid in Different Vanes Under Variable Residual Acceleration*, http://www.zarm.uni-bremen.de/2forschung/grenzph/isotermcap_rise/kapst_en.htm, ZARM—University of Bremen, printed Jun. 25, 2003, 2 pages.

Anonymous, *Draw—Up The Dream Stent*, Clinica 710, pp. 15 (Jun. 17, 1996), http://www.dialogweb.com/cgi/document?reg=1061848202959, printed Aug. 25, 2003, 2 pages.

Anonymous, *Coating Techniques, Air Knife Coating*, http://www.ferron-magnetic.co.uk/coatings/airknife.htm, printed Jul. 1, 2003, 1 page.

Anonymous, *Coating Techniques, Gap Coating* (Knife Over Roll, etc.), http://www.ferron-magnetic.co.uk/coatings.knife.htm, printed Jul. 1, 2003, 1 page.

Anonymous, *Coating Techniques, Gravure Coating*, http://www.ferron-magnetic.co.uk/coatings/gravure.htm, printed Jul. 1, 2003, 2 pages.

Anonymous, *Coating Techniques, Reverse Roll Coating*, http://www.ferron-magnetic.co.uk/coatings/revroll.htm, printed Jul. 1, 2003, 22 pages.

Anonymous, *Heparin-coated stents cut complications By 30%*, Clinica 732, pp. 17 (Nov. 18, 1996), http://www.dialogweb.com/cgi/document?reg=1061847871753, printed Aug. 25, 2003, 2 pages.

Anonymous, *Liquid Gravity Motor*, http://www.drspark86.com/idea001.html, printed Jun. 24, 2003, 2 pages (no date).

Anonymous, *Porosimetry—Why characterize the porosity?* 42 pages (no date).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting Continues to Dominate Cardiology*, http://www.dialogweb.com/cgi/document?req=1061848017752, Clinica vol. 720, pp. 22, (Sep. 2, 1996), printed Aug. 25, 2003, 2 pages.

Anonymous, *Surface Energy (Surface Wetting Capability)*, http://www.ndt-ed.org/EducationResources/CommunityCollege/PenetrantTest/PtMaterials/surfaceenergy.htm, printed Apr. 6, 2004, 3 pages (no date).

Anonymous, *The 14th International Young Physicists Tournament, The winning report*, Research Center for Quantum Information, Slovak Academy of Sciences, 5 pages (no date).

Anonymous, *The Wicking Well System*, http://www.decorative.com/wicking.html, printed June 24, 2003, 1 page.

Anonymous, *Typical Parylene Properties*, 3 pages (no date).

Anonymous, *Viscosity*, Commonwealth of Australia, 7 pages (no date).

Ansari, *End-to-End Tubal Anastomosis Using an Absorbable Stent*, Fertility and Sterility, vol. 32, No. 2, pp. 197-201 (Aug. 1979).

Ansari, *Tubal Reanastomosis Using Absorbable Stent*, International Journal of Fertility, vol. 23, No. 4, pp. 242-243 (1978).

Aoyagi et al., *Preparation of cross-linked aliphatic polyester and application to thermo-responsive material*, Journal of Controlled Release 32, pp. 87-96 (1994).

Barath et al., *Low Dose of Antitumor Agents Prevents Smooth Muscle Cell Proliferation After Endothelial Injury*, JACC vol. 3, No. 2, pp. 252A (Feb. 1989).

Barbucci et al., *Coating of commercially available materials with a new heparinizable material*, Journal of Biomedical Materials Research, vol. 25, pp. 1259-1274 (1991).

Beach et al., *Xylylene Polymers*, Encyclopedia of Polymer Science and Engineering, vol. 17, 2nd Edition, pp. 990-1025 (1989).

Boston Scientific, *Express 2™ Coronary Stent System*, http://www.bostonscientific.com/med_specialty/deviceDetail.jsp?task=tskBasicDevice.jsp&sectionId=4&relId=2,74,75,76&deviceId=11001&uniquedId=MPDB1180&clickType=endeca, printed Aug. 8, 2005, 1 page.

Bull, *Parylene Coating for Medical Applications*, Medical Product Manufacturing News, 2 pages (Mar.1993).

Casper et al., *Fiber-Reinforced Absorbable Composite for Orthopedic Surgery*, Polymeric Materials Science and Engineering, vol. 53, pp. 497-501(1985).

Charlson et al., *Temperature Selective Deposition of Parylene-C*, IEEE Transactions of Biomedical Engineering, vol. 39, No. 2, pp. 202-206 (Feb. 1992).

Chen et al., *The Kinetics of Wicking of Liquid Droplets into Yarns*, submitted to the Textile Research Journal, pp. 1-30 (Apr. 2001).

Chung et al., *Inner core segment design for drug delivery control of thermo-responsive polymeric micelles*, Journal of Controlled Release, vol. 65, pp. 93-103 (2000).

Crowe et al., *Absorption and Intestinal Metabolism of SDZ-RAD and Rapamycin in Rats*, Drug Metabolism and Disposition, vol. 27, No. 5, pp. 627-632 (1999).

De Scheerder et al., *Biocompatibility of polymer-coated oversized metallic stents implanted in normal porcine coronary arteries*, Atherosclerosis, vol. 114, pp. 105-114 (1995).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9, No. 6, pp. 495-504 Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis, vol. 34, pp. 272-278 (1995).

Devanathan et al., *Polymeric Conformal Coatings for Implantable Electronic Devices*, IEEE Transactions on Biomedical Engineering, vol. BME-27, No. 11, pp. 671-675 (1980).

Dichek et al., *Seeding of Intravascular Stents with Genetically Engineered Endothelial Cells*, Circulation, vol. 80, No. 5, pp. 1347-1353 (Nov. 1989).

Dreyer et al., *Critical Velocities in Open Capillary Flows*, pp. 604-609 (no date).

Duerig et al., *A comparison of balloon-and self-expanding stents*, Min. Invas. Ther. & Allied Technol., vol. 11, No. 4, pp. 173-178 (2002).

Dutkiewicz, *Some Advances in Nonwoven Structures for Absorbency, Comfort and Aesthetics*, AUTEX Research Journal, vol. 2, No. 3, pp. 153-165 (Sep. 2002).

EFD, *780S Series Spray Valves VALVEMATE™ 7040 Controller Operating Manual*, 24 pages (2002).

Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).

Elbert et al., *Conjugate Addition Reactions Combined with Free-Radical Cross-Linking for the Design of Materials for Tissue Engineering*, Biomacromolecules, vol. 2, pp. 430-441 (2001).

Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascular Prosthetic Materials*, J. Biomed. Mater. Res. vol. 10, pp. 113-122 (1976).

Eskin et al., *Tissue Cultured Cells: Potential Blood Compatible Linings for Cardiovascular Protheses*, Polymer Science and Technology, vol. 14, pp. 143-161 (no date).

Fischell et al., *Low-Dose, β-Particle Emission from 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx VELOCITY™ Stent*, 5 pages, Biocompatibles Ltd. (2001).

Gengenbach et al., *Evolution of the Surface Composition and Topography of Perflurinated Polymers Following mmonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol. 56, No. 3, pp. 353-360 (2002).

Gölander et al., *RF-Plasma-Modified Polystyrene Surfaces for Studying Complement Activation*, J. Biomater. Sci. Plymer Edn., vol. 4, No. 1 pp. 25-30 (1992).

Guidant, ACS RX Multi-Link ™Coronary Stent System, 6 pages (no date).

Guidant, Guidant Multi-Link Vision OTW Coronary Stent System, 2 pages (no date).

Hahn et al., *Biocompatibility of Glow-Discharge-Polmerized Films and Vacuum-Deposited Parylene*, Journal of Applied Polymer Science: Applied Polymer Symposium 38, 55-64 (1984).

Hahn et al., *Glow Discharge Polymers as Coatings for Implanted Devices*, John M. Dalton Research Center, University of Missouri-Columbia and the Graduate Center for Materials Research, pp. 109-113 (1981).

He et al., *Assessment of Tissue Blood Flow-Following Small Artery Welding with an Intraluminal Dissolvable Stent*, Microsurgery, vol. 19, No. 3, pp. 148-152 (1999).

Hehrlein et al., *Low-Dose Radioactive Endovascular Stents Prevent Smooth Muscle Cell Proliferation and Neointimal Hyperplasia in Rabbits*, Circulation, vol. 92, No. 6, pp. 1570-1575 (Sep. 15, 1995).

Helmus, *Overview of Biomedical Materials*, MRS Bulletin, pp. 33-38 (Sep. 1991).

Herdeg et al., *Antiproliferative Stent Coatings: Taxol and Related Compounds*,Semin. Intervent. Cardiol., vol. 3, pp. 197-199 (1998).

Hollahan et al., *Attachment of Amino Groups to Polymer Surfaces by Radiofrequency Plasmas*, Journal of Applied Polymer Science, vol. 13, pp. 807-816 (1969).

Huang et al., *Biodegradable Polymers Derived from Aminoacids*, Macromol. Symp. 144, 7-32 (1999).

Impulse Jetting, *About Us*, http://www.impulsejetting.com/about. html. printed Dec. 18, 2000, 1 page.

Impulse Jetting, *Our Technology*, http://www.impulsejetting.com/tech1.html, printed Dec. 18, 2000, 1 page.

Inagaki et al., *Hydrophilic Surface Modification of Polyethylene by No-Plasma Treatment*, Adhesion Sci. Technol., vol. 4, No. 2, pp. 99-107 (1990).

Inoue et al., *An AB block copolymer of oligo(methyl methacrylate) and poly(acrylic acid) for micellar delivery of hydrophobic drugs*, Journal of Controlled Release, vol. 51, pp. 221-229 (1998).

Itabashi et al., *Electroless Deposited CoWB for Copper Diffusion Barrier Metal*, International Interconnect Technology Conference, pp. 285-287 (2002).

Kataoka et al., *Block Copolymer Micelles as Vehicles for Drug Delivery*, Journal of Controlled Release vol. 24, pp. 119-132 (1993).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kelley et al., *Totally Resorbable High-Strength Composite Material*, Advances in Biomedical Polymers, vol. 35, pp. 75-85 (1987).

Klocke et al, *How Soil Holds Water* (G90-964), http://ianrpubs.unl.edu/fieldcrops/g964.htm, printed Apr. 6, 2004, 9 pages.

Konopka, *In-Plane Moisture Transport in Nonwovens*, Nonwovens Cooperative Research Center, NC State University, 56 pages.

Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).

Kubies et al., *Microdomain Structure In polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, 16 pages (1999).

Lambert et al., *Localized Arterial Wall Drug Delivery From a Polymer-Coated Removable Metallic Stent*, Circulation, vol. 90, No. 2, pp. 1003-1011 (Aug. 1994).

Levy et al., *Strategies For Treating Arterial Restenosis Using Polymeric Controlled Release Implants*, Biotechnology and Bioactive Polymers, pp. 259-268 (1994).

Liermann et al., *Prophylactic Endovascular Radiotherapy to Prevent Intimal Hyperplasia after Stent Implantation in Femoropopliteal Arteries*, CardioVascular and Interventional Radiology, vol. 17, pp. 12-16 (1994).

Liu et al., *Drug Release Characteristics of Unimolecular Polymeric Micelles*, Journal of Controlled Release, vol. 68, pp. 167-174 (2000).

Loeb et al., *Parylene as a Chronically Stable, Reproducible Microelectrode Insulator*, IEEE Transactions on Biomedical Engineering, Mar. 1977 (pp. 121-128).

Loh et al., *Plasma Enhanced Parylene Deposition*, Antec, pp. 1099-1103, 1991.

Machine Solutions, *FFS700 MSI Balloon Form/Fold/Set Equipment(PTCA), FFS800 MSI Balloon Form/Fold/Set Equipment (PTA)*, http://machinesolutions.orgffs7_8.html, printed Nov. 21, 2003 (2 pgs.).

Machine Solutions, *SC700 MSI Stent Crimping Equipment (PTCA), SC800 MSI Stent Crimping Equipment* (PTA), http://www.machinesolutions.org/sc7_8.html, printed Nov. 21, 2003, 2 pages.

Malik et al., *Development of an Energetic Ion Assisted Mixing and Deposition Process for $TIN_x$and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).

Malik et al., *Overview of plasma source ion implantation research at University of Wisconsin-Madison*, J. Vac. Sci. Technol. B, No. 12, vol. 2, pp. 843-849 (Mar./Apr. 1994).

Malik et al., *Sheath dynamics and dose analysis for planar targets in plasma source ion implantation*, Plasma Sources Sci. Technol. vol. 2, pp. 81-85 (1993).

Marconi et al., *Covalent bonding of heparin to a vinyl copolymer for biomedical applications*, Biomaterials, vol. 18, No. 12, pp. 885-890 (1997).

Matsumaru et al., *Embolic Materials For Endovascular Treatment of Cerebral Lesions*, J. Biomater. Sci. Polymer Edn., vol. 8, No. 7, pp. 555-569 (1997).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull., Vol. 33, No. 6, pp. 2490-2498 (1985).

Miyazawa et al., *Effects of Pemirolast and Tranilast on Intimal Thickening After Arterial Injury in the Rat*, J. Cardiovasc. Pharmacol., vol. 30, No. 2, pp. 157-162 (1997).

Moody, *Vacuum Coating Ultrasonic Transducers*, 1 page, Sensors (Dec. 1993).

Muller et al., *Advances in Coronary Angioplasty: Endovascular Stents*, Coronary Artery Disease, vol. 1, No. 4., pp. 438-448 (Jul./Aug. 1990).

Neimark et al., *Hierarchical Pore Structure and Wetting Properties of Single-Wall Carbon Nanotube Fibers*, Nano Letters, vol. 3, No. 3, pp. 419-423 (2003).

Nichols et al., *Electrical Insulation of Implantable Devices by Composite Polymer Coatings*, ISA Transactions, vol. 26, No. 4, pp. 15-18 (1987).

Nordrehaug et al., *A Novel Biocompatible Coating Applied to Coronary Stents*, EPO Heart Journal 14, p. 321 (P1694), Abstr. Suppl. (1993).

Nova Tran™ Custom Coating Services, *Parylene Conformal Coating*, 8 pages (no date).

Ohsawa et al., *Preventive Effects of an Antiallergic Drug, Pemirolast Potassium, on Restenosis After Percutaneous Transluminal Coronary Angioplasty*, American Heart Journal, vol. 136, No. 6, pp. 1081-1087 (Dec. 1998).

Olson, *Parylene, a Biostabel Coating for Medical Applications*, Specialty Coating Systems, Inc. Nova Tran™ Parylene Coating Services (no date).

Ozaki et al., *New Stent Technologies,*, Progress in Cardiovascular Diseases, vol. XXXIX, No. 2, pp. 129-140 (Sep./Oct. 1996).

Para Tech Coating Company, *Galxyl, Parylene Coatings by Para Tech*, 1 page (no date).

Para Tech Coating Company, *Lab Top® Parylene Deposition System*, 2 pages (no date).

Pechar et al., *Poly(ethylene glycol) Multiblock Copolymer as a Carrier of Anti-Cancer Drug Doxorubicin*, Bioconjucate Chemistry vol. 11, No. 2, pp. 131-139 (Mar./Apr. 2000).

Peng et al., *Role of polymers in improving the results of stenting in coronary arteries*, Biomaterial, vol. 17, pp. 685-694 (1996).

Peuster et al., *A novel approach to temporary stenting: degradable cardiovascular stents produced from corrodible metal-results 6-18 months after implantation into New Zealand white rabbits*, Heart vol. 86, pp. 563-569 (2001).

Pietrzak et al., *Bioabsorbable Fixation Devices: Status for the Craniomaxillofacial Surgeon*, Journal of Craniofacial Surgery, vol. 8, No. 2, pp. 92-96 (1997).

Pietrzak et al., *Bioresorbable Implants—Practical Considerations*, Bone, vol. 19, No. 1, Supplement, pp. 109S-119S (July 1996).

Poncin-Epaillard et al., *Reactivity of a Polypropylene Surface Modified in a Nitrogen Plasma*, Plasma Surface Modification of Polymers pp. 167-180 (1994).

Redman, *Clinical Experience with Vasovasostomy Utilizing Absorbable Intravasal Stent*, Urology, vol. XX, No. 11, pp. 59-61 (Jul. 1982).

Refraction Techonolgies, Corp., *Fine Bubble Diffusers*, 2 pages (do date).

Refraction Techonolgies, Corp., *Refractron Advanced Porous Ceramic Product Capabilities*, http://www.refractron.com/ecom/sp/cat=Product+Information, printed Apr. 6, 2004, 3 pages.

Rust et al., *The Effect of Absorbable Stenting on Postoperative Stenosis of the Surgically Enlarged Maxillary Sinus Ostia in a Rabbit Animal Model*, Archives of Otolaryngology, Head and Neck Surgery, vol. 122, pp. 1395-1397 (Dec. 1996).

Sadhir et al., *The Adhesion of Glow-Discharge Polymers, Silastic And Parylene to Implantable Platinum Electrodes: Results of Tensil Pull tests After Exposure to Isotonic Sodium Chloride*, Biomaterials, vol. 2, pp. 239-243 (Oct. 1981).

Saotome, et al., *Novel Enzymatically Degradable Polymers Comprising α-Amino Acid, 1,2-Ethanediol, and Adipic Acid*, Chemistry Letters, pp. 21-24, (1991).

Schatz, *A View of Vascular Stents*, Circulation, vol. 79, No. 2, pp. 445-457 (Feb. 1989).

Scheuer et al., *Model of plasma source ion implantation in planar, cylindrical, and spherical geometries*, J. Appl. Phys., vol. 67, No. 3, pp. 1241-1245 (Feb. 1990).

Schmidt et al., *Long-term Implants of Parylene-C Coated Microelectrodes*, Medical & Biological Engineering & Computing, pp. 96-101 (Jan. 1988).

Serkova et al., *Tissue Distribution and Clinical Monitoring of the Novel Macrolide Immunosuppressant SDZ-RAD and its Metabolites in Monkey Lung Transplant Receipients: Interaction with Cyclosporine*, The Journal of Pharmacology and Experimental Therapeutics, vol. 294, No. 1, pp. 323-332 (2000).

Serruys et al., *I Like the Candy, I Hate the Wrapper; the $^{32}P$ Radioactive Stent*, Circulation, vol. 101, pp. 3-7 (Jan. 2000).

Shamim et al., *Measurements of Spatial and Temporal Sheath Evolution for Spherical and Cylindrical Geometrics in Plasma Source Ion Implantation*, J. Appl. Phys., vol. 69, No. 5, pp. 2904-2908 (Mar. 1991).

Shigeno, *Prevention of Cerebrovascular Spasm By Bosentan, Novel Endothelin Receptor*, Chemical Abstract 125:21230 (1996).

Sono Tek Corporation, *AccuMist™ for Single Stent Coating Applications*, http://www.sono-tek.com/biomedical/accumist_stent.html, printed Aug. 2, 2005, 3 pages.

Sono Tek Corporation, *MediCoat™ DES 1000, Benchtop Stent Coating System*, http://www.sono-tek.com/biomedical/medicoat_standalone.html, printed Aug. 2, 2005, 4 pages.

Sono Tek Corporation, *MicroMist for Stent Coating*, http://www.sono-tek.com/biomedical/micromist_stent.html, printed Aug. 2, 2005, 3 pages.

Specialty Coating Systems, Inc., *The Parylene Press*, 4 pages (Summer 1993).

Specialty Coating Systems, Inc., *The Parylene Press*, 6 pages (Spring 1993).

Specialty Coating Systems, Inc., *The Parylene Press*, 7 pages (Winter 1992).

Specialty Coating Systems, *Parylene and Nova Tran™ Parylene Coating Services, for Unmatched Conformal Coating Performance*, 21 pages (no date).

Specialty Coating Systems, *Parylene, a Biostable Coating for Medical Applications*, 6 pages (no date).

Specialty Coating Systems, *Repair and Recoating of Parylene Coated Printed Circuit Boards*, 15 pages (no date).

Straube, *Moisture, Materials, & Buildings*, HPAC Engineering, pp. 2-7 (no date).

Taher, *Capillary interaction between a small thin solid plate and a liquid*, Mechanical and Industrial Engineering, University of Illinois at Urbana-Champaign, 4 pages (undated).

Tamai et al., *Initial and 6-Month Results of Biodegradable Poly-l-Lactic Acid Coronary Stents in Humans*, Circulation, vol. 102, pp. 399-404 (2000).

Trident, Inc., http://www.tridentintl.com/subbody.html, printed Dec. 18, 2000, 1 page.

Trident, Inc., *Product Lines*, http://www.tridentintl.com/products-apps/ultrajet.html, printed Dec. 18, 2000, 3 pages.

Tsuji et al., *Biodegradable Polymeric Stents*, Current Interventional Cardiology Reports vol. 3, pp. 10-17 (2001).

Union Carbide Adhesion Promoters,*Union Carbide A-174 Silane*, 5 pages (Jan. 1968).

Union Carbide Electronics Division, *Parylene Environmentally Compatible Conformal Coatings for Electronic Components Assemblies and Precision Parts*, 14 pages (no date).

Union Carbide, *Abrasion Resistance of Parylene and Other Conformal Circuit Board Coatings*, Parylene Products, No. 4, 13 pages (Oct. 1977).

Union Carbide, *Adhesion Promotion Systems for Parylene*, Parylene Products, No. 15, Revision 1, 8 pages (Oct. 1977).

Union Carbide, *Adhesion Promotion Systems for Parylene*, Technology Letter, No. 15, 13 pages (Oct. 1975).

Union Carbide, *Evaluation of Parylene and Other Pellicles as Beam Splitters*, Parylene Products, No. 8, Edited, 19 pages (Oct. 1977).

Union Carbide, *Fluorescent Parylene Coatings*, Parylene Products, No. 7 Revision 1, 8 pages (Oct. 1977).

Union Carbide, *Fluorescent Parylene Coatings*, Technology Letter, No. 7, 8 pages (Oct. 1973).

Union Carbide, *Mechanical Protection Criteria for Thin Conformal Coatings*, Parylene Products, No. 3, 21 pages (Oct. 1977).

Union Carbide, *Method for Repair and Patching of Parylene Coated Printed Circuit Boards*, Parylene Products, No. 2 Revision 1, 9 pages (Oct. 1977).

Union Carbide, *Microencapsulation by Vapor Deposition*, Parylene Products, No. 6, 12 pages (Oct. 1977).

Union Carbide, *MIL I 46058, Qualification of Parylene N, C, and D*, Parylene Products, No. 1 Revision 2, 8 pages (Oct. 1977).

Union Carbide, *Parylene Bibliography*, Parylene Products, No. 5, Revision 4, 17 pages (Jan. 18, 1982).

Union Carbide, *Parylene Conformal Coatings for Hybrid Microelectronics*, Parylene Products, No. 9, 23 pages (Oct. 1973).

Union Carbide, *Parylene Pellicles for Space Applications*, Parylene Products, No. 10, 50 pages (Oct. 1977).

Union Carbide, *Parylene Pyrolysis Kinetics*, Parylene Products, No. 11, 12 pages (Oct. 1977).

Union Carbide, *Parylene Pyrolysis Kinetics*, Technology Letter, No. 11, 12 pages (May 1974).

Union Carbide, *Parylene Removal with Oxygen Plasmas*Parylene Products, No. 18, 7 pages (Aug. 1977).

Union Carbide, *Printed Circuit Board Masking Techniques for Use with Parylene*, No. 14, Revision 1, 11 pages (Oct. 1977).

Union Carbide, *Solvent Resistance of the Parylenes*, Parylene Products, No. 12, Revision 1, 5 pages (Oct. 1977).

Union Carbide, *The Selective Removal of Parylene By Plasma Etching*, No. 13, Revision 1, 7 pages (Oct. 1977).

Union Carbide, *Thermal Endurance of the Parylenes in Air*, Parylene Products, No. 16, 4 pages (Mar. 1976).

Union Carbide, *Vapor Phase Adhesion Promotion Systems*, Parylene Products, No. 17, Revision 1, 11 pages (Oct. 1977).

van Beusekom et al., *Coronary Stent Coatings*, Coronary Artery Disease, vol. 5, No. 7, pp. 590-596 (Jul. 1994).

van der Giessen et al., *"Edge Effect" of $^{32}P$ Radioactive Stents is Caused by the Combination of Chronic Stent Injury and Radioactive Dose Falloff*, Circulation, vol. 104, pp. 2236-2241 (Oct. 30, 2001).

Vapor Inc., *Vapore-Jet™ Capillary Pump—How it Works*, http://www.vapore.com/tech_howto.htm, printed Aug. 13, 2003, 2 pages.

von Recum et al., *Degradation of polydispersed poly(L-lactic acid)to modulate lactic acid release*, Biomaterials, vol. 16, pp. 441-445 (1995).

Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).

Wilensky et al., *Methods and Devices for Local Drug Delivery in Coronary and Peripheral Arteries*, Trends Cardiovasc. Med., vol. 3, No. 5, pp. 163-170 (1993).

Wong et al., *An Update on Coronary Stents*, Cardio, 8 pages (Feb. 1992).

World Precision Instruments, Inc., *Nanoliter Injector*, http://www.wpiinc.com/WPI_Web/Microinjection/Nanoliter_Injector.html, printed Jun. 10, 2005, 3 pages.

World Precision Instruments, Inc., *Nanoliter Injector*, http://www.wpi-europe.com/products/microinjection/nanoliter.htm printed Jun. 10, 2005, 2 pages.

World Precision Instruments, Inc., *Pneumatic PicoPumps*, http://www.wpieurope.com/products/microinjection/picopumps.htm, printed Jun. 10, 2005, 4 pages.

World Precision Instruments, Inc., *Pneumatic PicoPumps*, http://www.wpiinc.com/WPI_Web/Microinjection/Pneumatic_PicoPumps.html, printed Jun. 10, 2005, 4 pages.

Yau et al., *Modern Size-Exclusion Liquid Chromatography*, Wiley-Interscience Publication, 9 pages (1979).

Yokoyama et al., *Characterization of physical entrapment and chemical conjugation of adriamycin in polymeric micelles and their design for in vivo delivery to asolid tumor*, Journal of Controlled Release, vol. 50, pp. 79-92 (1998).

Yuen et al., *Tissue response to potential neuroprosthetic materials implanted subdurally*, Biomaterials, vol. 8, pp. 57-62 (Mar. 1987).

Zhmud et al., *Dynamics of Capillary Rise*, Journal of Colloid and Interface Science, vol. 228, pp. 263-269 (2000).

Zimarino et al., *Analysis of Stent Edge Restenosis with Different Forms of Brachytherapy*, The American Journal of Cardiology, vol. 89, pp. 322-325 (Feb. 1, 2002).

Zylberman et al., *Comparative Study of Electroless Co(W,P) and Co(Mo,P) Thin-Films for Capping and Barrier Layers for Cu Metallization*, 2002 Advanced Metallization Conference, 2 pages (no date).

U.S. Appl. No. 10/255,913, filed Sep. 26, 2002, Tang et al.

U.S. Appl. No. 10/304,669, filed Oct. 25, 2002, Madriaga et al.

U.S. Appl. No. 10/317,435, filed Dec. 11, 2002, Hossainy et al.

U.S. Appl. No. 10/322,255, filed Dec. 17, 2002, Chen et al.

Katsarava et al., Amino Acid-Based Bioanalogous Polymers, Synthesis, and Study of Regular Poly(ester amide)s Based on Bis($\alpha$-amino acid)$\alpha$, w-Alkylene Diesters, and Aliphatic Dicarbolic Acids, Journal of Polymer Science, Part A; Polymer Chemistry, vol. 37, 391-407 (1999).

Refraction Technologies Corp., http://www.refractron.com/ecom/sp/cat=Custom+Applications, printed Jun. 24, 2003, 1 page.

Shamim et al., Measurement of electron emission due to energetic ion bombardment in plasma source ion implantation, J. Appl. Phys., vol. 70, No. 9, pp. 4756-4759 (Nov. 1991).

World Precision Instruments, Inc., http://www.wpiinc.com/WPI_Web/Pumps/pneumatic_Fig.gif, printed Sep. 30, 2002, 1 page.

\* cited by examiner

US 7,258,891 B2

STENT MOUNTING ASSEMBLY AND A METHOD OF USING THE SAME TO COAT A STENT

CROSS REFERENCE

This is a divisional application of U.S. Ser. No. 09/896,436, which was filed on Jun. 28, 2001 and issued as U.S. Pat. No. 6,565,659.

BACKGROUND OF THE INVENTION

1. Field of the Invention

This invention relates to a stent mounting device and a method of coating a stent using the device.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Thus, it is desirable to minimize the amount of coating material that is deposited on the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY OF THE INVENTION

The present invention provides an apparatus for supporting a stent. The apparatus includes a mounting assembly for supporting a stent during a process of applying a coating substance to the stent. The mounting assembly prevents the formation of the coating or at least minimizes the amount or thickness of the coating that can be formed on the regions of the stent where the mounting assembly is in contact with the stent.

In one embodiment, the mounting assembly includes a mounting member for supporting the stent and a shield member for providing a barrier between a selected area of the stent and a coating applicator. In another embodiment, the mounting assembly includes a first member for supporting the stent at a first end, a second member for supporting the stent at a second end, a third member connecting the first member to the second member and extending through the longitudinal bore of the stent, and a shield member for providing a barrier between a selected area of the stent and a coating applicator.

In still another embodiment, the mounting assembly includes a shielding member capping over one end of the stent without being in contact with the surface of the stent. In another embodiment, the mounting assembly includes a mounting member for supporting the stent and a shield member supported by the mounting member for creating a barrier between a portion of the stent and a coating applicator. In such an embodiment, the position of the shield member on the mounting member can be adjusted so as to allow a user to modify the area over which the shield member covers the stent.

In yet another embodiment, the mounting assembly includes a first member having a first coning end that can be at least partially inserted within a first end of the stent and a second member having a second coning end that can be at least partially inserted within an opposing second end of the stent, the coning ends being in contact with the ends of the stent. In such an embodiment, the mounting assembly further includes a third member connecting the first member to the second member and shielding members supported by the first and second members for reducing or eliminating the amount of the coating substance that is applied to the first and second ends of the stent.

Also provided is an assembly for supporting a stent during the coating process. The assembly includes means for minimizing or eliminating the amount of coating material that can be applied to a designated area of the stent during the coating process. In one embodiment, the means is defined by a hollow body capable of surrounding a region of the stent without being in contact with the surface of the stent. In another embodiment, the amount of coating material can be minimized or eliminated at the regions where the stent is in contact with the assembly.

The present invention additionally provides a method of coating a stent. The method includes mounting a stent on a support assembly, wherein the support assembly is configured to reduce or eliminate the amount of coating that is applied to the regions where the stent is in contact with the support assembly. The method also includes applying a coating material to the stent for forming a coating.

In one embodiment, the act of applying includes spraying the coating material onto the stent. In another embodiment, the act of applying a coating includes applying the coating material to a stent while rotating the stent about the longitudinal axis of the stent. In another embodiment, the act of applying a coating includes applying the coating material to a stent while moving the stent in a linear direction about the longitudinal axis of the stent.

DETAILED DESCRIPTION

Embodiments of the Mounting Assembly

Figure 1:
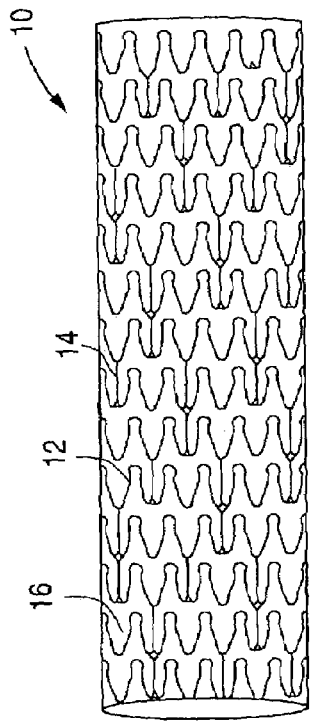
FIG. 1 illustrates a conventional stent.
Figure 2A:
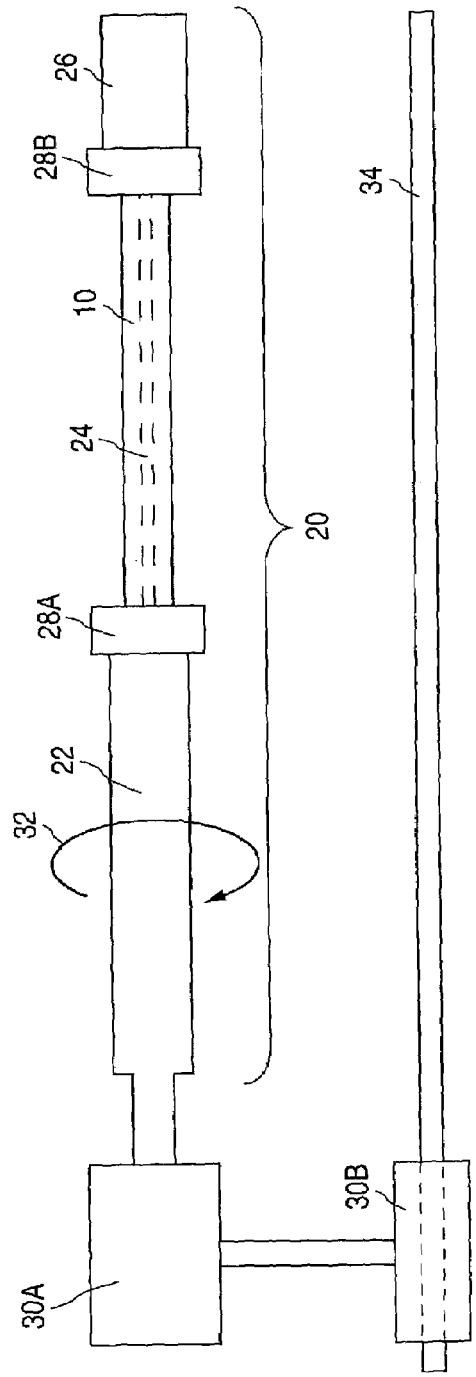
FIG. 2A illustrates a mounting assembly for supporting a stent.

Referring to FIG. 2A, a mounting assembly 20 for supporting stent 10 is illustrated to include a support member 22, a mandrel 24, a lock member 26, and shields 28A and 28B. Support member 22 can connect to a motor 30A so as to provide rotational motion about the longitudinal axis of stent 10, as depicted by arrow 32, during the coating process. Another motor 30B can also be provided for moving support member 22 in a linear direction, back and forth, along a rail 34.

Figure 2B:
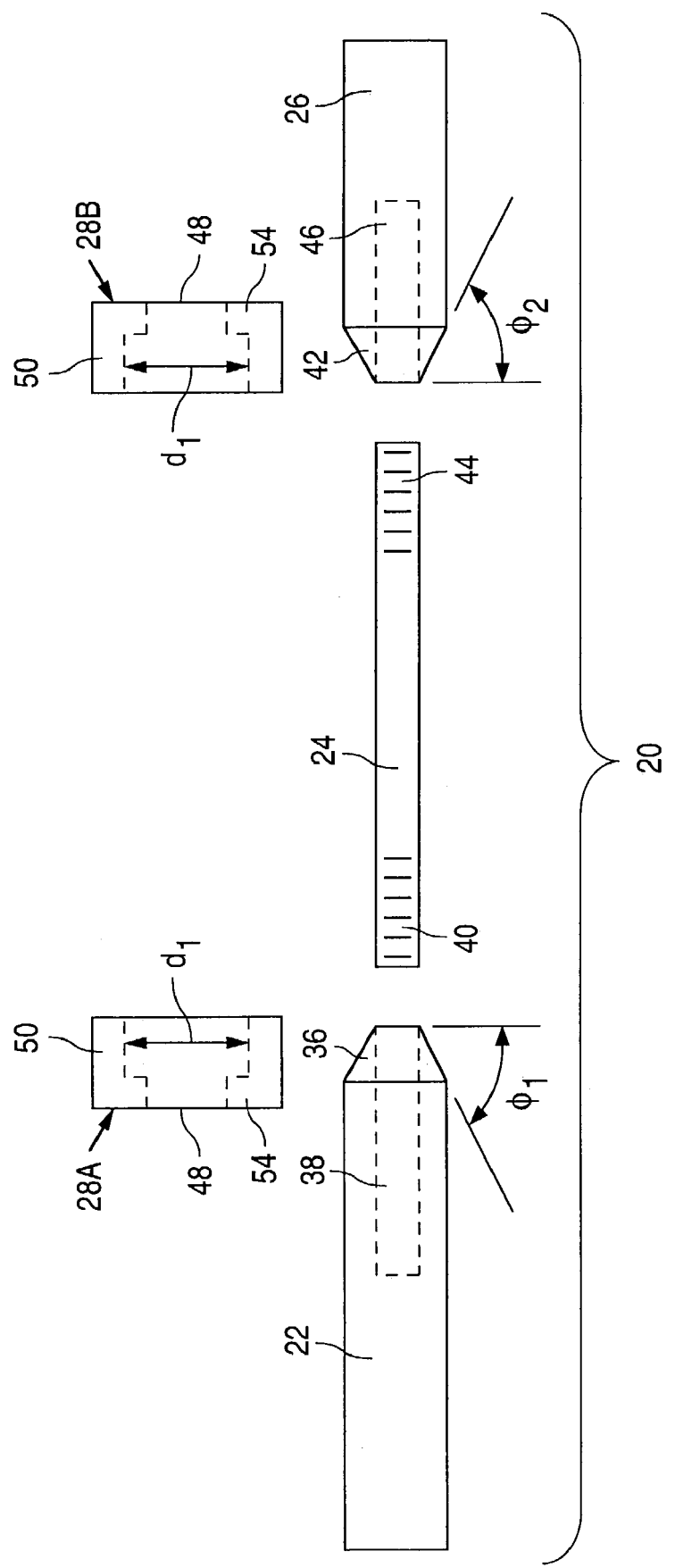
FIG. 2B illustrates an expanded view of the mounting assembly in accordance with one embodiment of the present invention.

Referring to FIG. 2B, support member 22 includes a coning end portion 36, tapering inwardly at an angle $\phi_1$ of about 15° to about 75°, more narrowly from about 30° to about 60°. By way of example, angle $\phi_1$ can be about 45°. In accordance with one embodiment, mandrel 24 can be permanently affixed to coning end portion 36. Alternatively, support member 22 can include a bore 38 for receiving a first end 40 of mandrel 24. First end 40 of mandrel 24 can be threaded to screw into bore 38 or, alternatively, can be retained within bore 38 by a friction fit. Bore 38 should be deep enough so as to allow mandrel 24 to securely mate with support member 22. The depth of bore 38 can also be over-extended so as to allow a significant length of mandrel 24 to penetrate or screw into bore 38. Bore 38 can also extend completely through support member 22. This would allow the length of mandrel 24 to be adjusted to accommodate stents of various sizes.

The outer diameter of mandrel 24 can be smaller than the inner diameter of stent 10 so as to prevent the outer surface of mandrel 24 from making contact with the inner surface of stent 10. A sufficient clearance between the outer surface of mandrel 24 and the inner surface of stent 10 should be provided to prevent mandrel 24 from obstructing the pattern of the stent body during the coating process. By way of example, the outer diameter of mandrel 24 can be from about 0.010 inches (0.254 mm) to about 0.017 inches (0.432 mm) when stent 10 has an inner diameter of between about 0.025 inches (0.635 mm) and about 0.035 inches (0.889 mm).

Lock member 26 includes a coning end portion 42 having an inwardly tapered angle $\phi_2$. Angle $\phi_2$ can be the same as or different than the above-described angle $\phi_1$. A second end 44 of mandrel 24 can be permanently affixed to lock member 26 if end 40 is disengagable from support member 22. Alternatively, in accordance with another embodiment, mandrel 24 can have a threaded second end 44 for screwing into a bore 46 of lock member 26. Bore 46 can be of any suitable depth that would allow lock member 26 to be incrementally moved closer to support member 22. Bore 46 can also extend completely through lock member 26. Accordingly, stents 10 of any length can be securely pinched between support and lock members 22 and 26. In accordance with yet another embodiment, a non-threaded second end 44 and bore 46 combination is employed such that second end 44 can be press-fitted or friction-fitted within bore 46 to prevent movement of stent 10 on mounting assembly 20.

Figure 3:
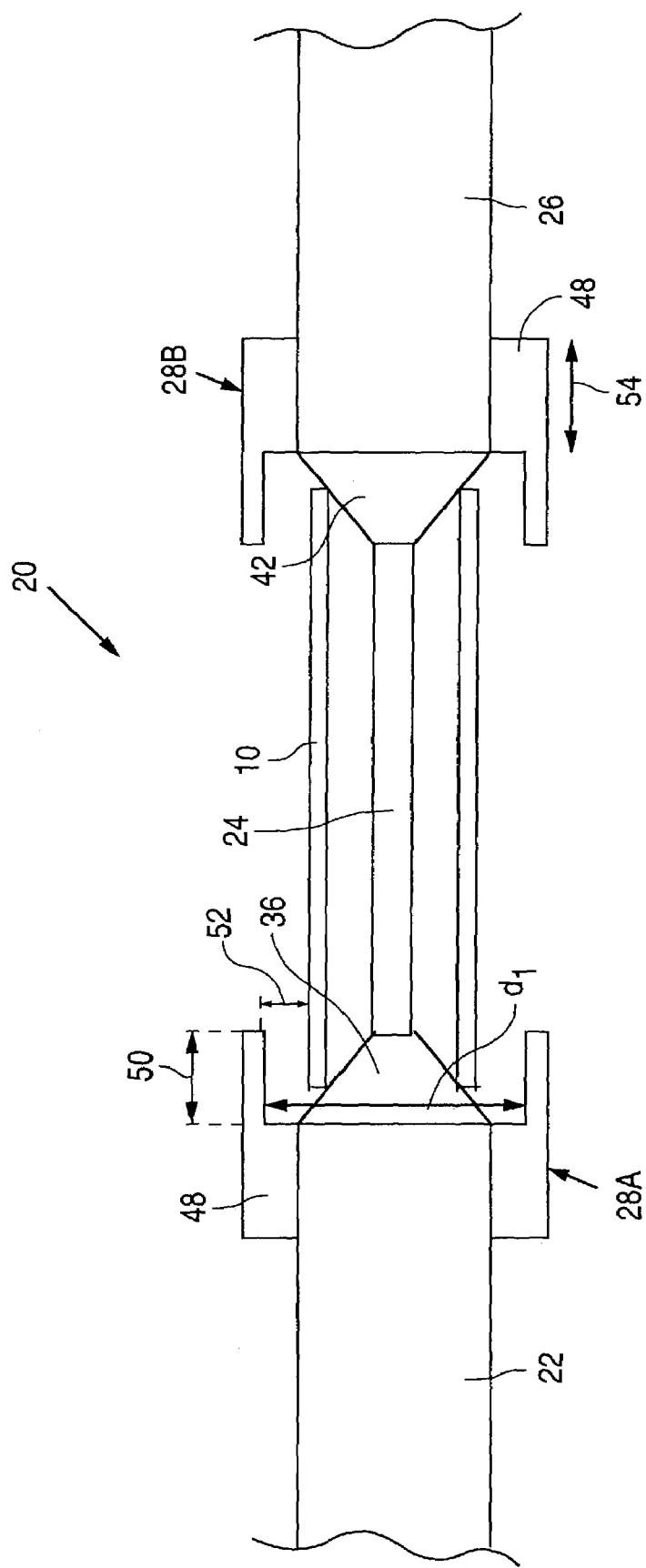
FIG. 3 is a cross-sectional view of the interface between the mounting assembly and the stent.

Mounting assembly 20 supports stent 10 via coning end portions 36 and 42. FIG. 3 illustrates the interface between coning end portions 36 and 42 and the opposing ends of stent 10 so as to provide minimal contact between stent 10 and mounting assembly 20. Opposing forces exerted from support and lock members 22 and 26, for securely pinching stent 10, should be sufficiently strong so as to prevent any significant movement of stent 10 on mounting assembly 20. However, the exerted force should not compress stent 10 so as to distort the body of stent 10. Over or under application of support force can lead to coating defects, such as non-uniformity of the coating thickness.

Shields 28A and 28B provide a circumferential barrier around the peripheral ends of stent 10, particularly over the area where stent 10 is in physical contact with coning end portions 36 and 42. Shields 28A and 28B can be permanently affixed to support member 22 and/or lock member 26. Alternatively, in a more useful commercial embodiment, shields 28A and 28B can be adjustably supported by members 22 and/or 26.

In one embodiment, shields 28A and 28B can be defined by a hollow body 48 having a first section or overhang 50 that is configured to extend over at least a portion of stent 10. Overhang 50 should have an inner diameter $d_1$ that is larger than the outer diameter of stent 10, in a mount position on mounting assembly 20, so as to create a sufficient gap 52 between shields 28A and 28B and the outer surface of stent 10 for eliminating any contact with the deposited coating. Gap 52 can be from about 0.003 inches (0.08 mm) to about 0.08 inches (about 2.03 mm), typically about 0.04 inches (about 1.02 mm), in measurement. Care should be taken, however, to ensure that gaps 52 are not so large as to allow the composition to access the stent 10-mounting assembly 20 interface.

Hollow body 48 can also include a second section 54 for adjustably receiving the non-coned portions of members 22 and 26. For example, second section 54 and non-coned portions of support and lock members 22 and 26 can be threaded such that the clockwise or counterclockwise rotation of shields 28A and 28B would allow the user to move shields 28A and 28B towards or away from stent 10. Thus, the area over stent 10 that is sheltered by overhang 50 can be adjusted. Hollow body 48 and second section 54 can also be integral parts of the non-coned portions of support and lock members 22 and 26.

Shields 28A and 28B function to minimize coating defects at the ends of stent 10 by limiting or eliminating the application of the coating substance to the ends of stent 10. The presence of shields 28A and 28B causes the coating to be thinner (or completely eliminated) on the surface of stent 10 over which shields 28A and 28B are hung, as compared to the surface of stent 10 that is not screened by shields 28A and 28B. Accordingly, the area of stent 10 over which shields 28A and 28B are extended should be selected to yield a suitable balance between reduction of the potential for coating defects at the ends of stent 10 and uniformity of the coating thickness. Further, appropriate selection of gap 52 and overhang 50, taking into account the distance between the spray nozzle and stent 10, can facilitate a gradual decrease in the coating thickness at the ends of stent 10 beneath overhang 50 as opposed to an abrupt void of coating near the shielded stent ends.

Coating a Stent Using the Mounting Assembly

The following method of application is being provided by way of illustration and is not intended to limit the embodiments of mounting assembly 20 of the present invention. A spray apparatus, such as EFD 780S spray device with VALVEMATE 7040 control system (manufactured by EFD Inc., East Providence, R.I.), can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition.

During the application of the composition, a stent supported by mounting assembly 20 can be rotated about the stent's central longitudinal axis. Rotation of the stent can be from about 1 rpm to about 300 rpm, more narrowly from about 50 rpm to about 150 rpm. By way of example, the stent can rotate at about 120 rpm. The stent can also be moved in a linear direction along the same axis. The stent can be moved at about 1 mm/second to about 12 mm/second, for example about 6 mm/second, or for a minimum of at least two passes (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/cm$^2$ (of stent surface) to about 10 micrograms/cm$^2$, for example less than about 2 micrograms/cm$^2$ per 5-second spray.

Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2–4 hours) or by the application of warm air. The application of warm air between each repetition minimizes coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer in a single repetition can, however, cause coating defects.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

In accordance with one embodiment, the composition can include a solvent and a polymer dissolved in the solvent and optionally a wetting fluid. The composition can also include active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(etheresters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

Wetting fluid can be used to enhance the wetting of the composition or to increase the capillary permeation of the composition. Capillary permeation is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of wetting fluid include tetrahydrofuran (THF), dimethylformamide (DMF), 1-butanol, and n-butyl acetate.

The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, WI 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany), methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrins, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a stent, comprising:
   mounting a stent on a support assembly;
   positioning a shielding member to cover a selected portion of the stent without the shielding member being in contact with the stent, wherein the shielding member is configured to reduce or eliminate coating material applied to the selected portion of the stent; and
   applying a coating material to the stent for forming a coating.

2. The method of claim 1, wherein the act of applying comprises spraying the coating material onto the stent.

3. The method of claim 1, wherein the act of applying comprises spraying the coating material onto the stent, the coating material including a polymer added to a fluid and optionally a therapeutic substance added thereto.

4. The method of claim 1, wherein the act of applying comprises applying the coating material to the stent while rotating the stent about a longitudinal axis of the stent.

5. The method of claim 1, wherein the selected portion of the stent is a region of the stent in contact with the support assembly.

6. The method of claim 1, wherein the shielding member is rotatably integrated with the support assembly such that rotation of the shielding member moves the shielding member relative to the support assembly.

7. A method of coating a stent, comprising:
   mounting a stent on a support assembly;
   spraying via a spray nozzle a coating composition onto the stent; and
   positioning a shielding member between the stent and the spray nozzle to shield a selected portion of the stent during the spraying of the coating composition such that the shielding member does not make contact with the stent.

8. The method of claim 7, wherein the selected portion of the stent is the region where the support assembly is in contact with the stent.

9. The method of claim 7, wherein the positioning of the shielding member comprises moving the shielding member along the length of the stent so that the shielding member covers the selected portion of the stent.

10. The method of claim 7, wherein the shielding member is rotatably integrated with the support assembly such that rotation of the shielding member moves the shielding member relative to the support assembly.

11. A method of coating a stent, comprising:
positioning a stent on a support assembly such that at least a segment of the stent is inserted into a hollow tubular body that is adjustably integrated with the support assembly, the hollow tubular body adapted to reduce an amount of or prevent a coating composition from being applied to an area of the stent covered by the tubular body;
adjusting the position of the hollow tubular body over the stent to an area which a user wants to cover by a means for adjusting the position; and
applying a coating composition to the stent.

12. A method of coating a stent, comprising:
positioning a stent on a support assembly such that at least a segment of the stent is inserted into a hollow tubular body that is adjustably integrated with the support assembly, the hollow tubular body adapted to reduce an amount of or prevent a coating composition from being applied to an area of the stent covered by the tubular body, wherein the hollow tubular body does not make contact with the stent;
adjusting the position of the hollow tubular body over the stent to an area which a user wants to cover; and
applying a coating composition to the stent.

13. The method of claim 12, wherein the hollow tubular body is rotatably integrated with the support assembly such that rotation of the hollow tubular body moves the hollow tubular body relative to the support assembly.

14. A method of coating a stent, comprising:
positioning a stent on a support assembly;
positioning a shield between a nozzle assembly and the stent so that the shield does not make contact with the stent, wherein the position of the shield is adjustable with respect to the support assembly; and
applying a coating composition to the stent.

15. The method of claim 14, wherein the shield circumscribes a segment of the length of the stent.

16. The method of claim 14, wherein the shield is adjustably integrated with the support assembly.

17. The method of claim 14, wherein the shield has a hollow tubular body in which the stent can be inserted.

18. The method of claim 14, wherein the shield is rotatably integrated with the support assembly such that rotation of the shield moves the shield relative to the support assembly.

19. A method of coating a stent, comprising applying a coating composition on a stent, positioned on a support assembly, by a nozzle such that a shield member positioned between the nozzle and an outer surface of the stent reduces an amount of or prevents the coating composition from being applied on an outer surface of the stent underneath the shield member, wherein the shield member does not make contact with the outer surface of the stent underneath the shield member during the application of the coating composition.

20. The method of claim 19, wherein the shield member is adjustably integrated with the support assembly.

21. The method of claim 19, additionally comprising rotating the stent during the application of the coating composition.

22. The method of claim 19, additionally comprising moving the shield member to a position prior to application of the coating composition.

* * * * *